US006818757B2

(12) United States Patent
Lee et al.

(10) Patent No.: US 6,818,757 B2
(45) Date of Patent: Nov. 16, 2004

(54) CARDIAC-CELL SPECIFIC ENHANCER ELEMENTS AND USES THEREOF

(75) Inventors: Ike W. Lee, Norwood, MA (US); Seigo Izumo, Brookline, MA (US)

(73) Assignee: Beth Israel Deaconess Medical Center, Boston, MA (US)

(*) Notice: Subject to any disclaimer, the term of this patent is extended or adjusted under 35 U.S.C. 154(b) by 0 days.

(21) Appl. No.: 09/761,466

(22) Filed: Jan. 16, 2001

(65) Prior Publication Data

US 2002/0022259 A1 Feb. 21, 2002

Related U.S. Application Data

(60) Provisional application No. 60/176,419, filed on Jan. 14, 2000.

(51) Int. Cl.$^7$ .......................... C07H 21/04; C12N 15/63
(52) U.S. Cl. ................... 536/24.1; 536/23.1; 435/320.1
(58) Field of Search .............................. 536/23.1, 24.1; 435/320.1

(56) References Cited

FOREIGN PATENT DOCUMENTS

WO    WO 96/02552    1/1996

OTHER PUBLICATIONS

Chen et al., "Identification of Novel DNA Binding Targets and Regulatory Domains of a Murine Tinman Homeodomain Factor, nkx–2.5" *J. Biol. Chem.* 270:15628–15633 (1995).
Doe Joint Genome Institute, Database Genbank, Accession No. AC008412 (2000).
Edmondson et al., "Mef2 Gene Expression Marks the Cardiac and Skeletal Muscle Lineages During Mouse Embryogenesis" *Development* 120:1251–1263 (1994).
Fishman et al., "Parsing the Heart: Genetic Modules for Organ Assembly" *Cell* 91:153–156 (1997).
Heikinheimo et al., "Localization of Transcription Factor GATA–4 to Regions of the Mouse Embryo Involved in Cardiac Development" *Dev. Biol.* 164:361–373 (1994).
Kelley et al., "GATA–4 is a Novel Transcription Factor Expressed in Endocardium of the Devloping Heart" *Development* 118:817–827 (1993).
Komura et al., "Csx: A Murine Homebox–Containing Gene Specifically Expressed in the Developing Heart" *Proc. Natl. Acad. Sci. USA* 90:8145–8149 (1993).

Lamerdin et al., "Sequence Analysis of a 3.5 Mb Contig in Human 19p 13.3 Containing a Serine Protease Gene Cluster" Database Genbank, Accession No. AC006505 (1999).
Lints et al., "Nkx–2.5: A Novel Murine Homebox Gene Expressed in Early Heart Progenitor Cells and Their Myogenic Descendants" *Development* 119:419–431 (1993).
Lyons, "Vertebrate Heart Development" *Curr. Opin. Genet. Dev.* 6:454–460 (1996).
Mohun et al., "Early Steps in Vertebrate Cardiogenesis" *Curr. Opin. Genet. Dev.* 7:628–633 (1997).
Oka et al., "Autoregulation of Human Cardiac Homebox Gene CSX1: Mediation by the Enhancer Element in the First Intron" *Heart Vessels* 12:10–14 (1997).
Olson et al., "Molecular Pathways Controlling Heart Development" *Science* 272:671–676 (1996).
Schwartz et al., "Building the Heart Piece by Piece: Modularity of cis–elements Regulating Nkx2–5 Transcription" *Development* 126:4187–4192 (1999).
Shiojima et al., "Molecular Cloning and Characterization of Human Cardiac Homebox Gene CSX1" *Circ. Res.* 79:920–929 (1996).
Strausberg, "National Cancer Institute, Cancer Genome Anatomy Project (CGAP), Tumor Gene Index" Database Genbank, Accession No. AA994279 (1998).
Tanaka et al., "Complex Modular cis–acting Elements Regulate Expression of the Cardiac Specifying Homebox Gene Csx/Nkx2.5" *Development* 126:1439–1450 (1999).
Tanaka et al., "Vertebrate Homologs of Tinman and Bagpipe: Roles of the Homebox Genes in Cardiovascular Development" *Dev. Genet.* 22:239–249 (1998).
Turbay et al., "Molecular Cloning, Chromosomal Mapping, and Characterization of the Human Cardiac–Specific Homebox Gene hCsx" *Molec. Med.* 2:86–96 (1996).
GenBank Accession No. AC008412.1, DOE Joint Genome Institute, submitted Aug. 3, 1999.
GenBank Accession No. AC008412.2, DOE Joint Genome Institute, submitted Aug. 3, 1999, replaced AC008412.1 on Dec. 18, 1999.

*Primary Examiner*—Anne-Marie Faulk
*Assistant Examiner*—Celine Qian
(74) *Attorney, Agent, or Firm*—Clark & Elbing, LLP

(57) ABSTRACT

The invention features cardiac cell-specific enhancer elements derived from Csx/Nkx2.5 regulatory regions. These enhancer elements are useful, for example, for (i) regulating gene expression in cardiac cells, (ii) inducing stem cells (e.g., embryonic stem cells or bone marrow stem cells) to differentiate as cardiomyocytes, and (iii) identifying factors that induce the differentiation of stem cells as cardiomyocytes.

12 Claims, 20 Drawing Sheets

FIG. 4A (1)

CTCGAGCCCAGGAGTTCAAGACCAGCCTGGGAAACATAGGGAGACCCC
TCTCTCTCCACAAAAAATTTAAAAACTAGCCAGGTGTGGTGGCAAACA
CCTGTAGTCCCAGCTACTCAGAAGGCTGAGGTGGGAGGATCACTTGAG
CCTGGAAAGTAGAGGCTACAGTGAGCCGTGATCACACCACTGCACTCC
AGCCTGGGAGACAGAGTGAGACCCTGTCAAATAAATAAACAAACAAAT
AATGATTAAAATAACTAAAACTAATTTTATGCTATTTTCACCTTGTAT
TTTGTAAAGATTTTTAAAATGAAAATTCCCAAATTGCTTTCCAGAAGG
ATTGTTCAAAATTATACCCACATTTCACTCATGTTCTCTTCCTGAACA
GCAGCAATCAGGAAAAACTCCCTGGAAGAGGCAGGGCTTAGACTGAGA
TTTTAAAAGGGGGTAGGCCTCAGCTCTCCTTCCAGGTTTACACTGTGC
ATGTTTCCAAACTCAAAGAATTTACACTCTTCTGGTTGCATTGCTCTG
TAAAGATCTGACCCACTACTATGTATTAAAAAGGGATGCATGATAATG
AATTCAGCCCTCTCTGTAAAATCCAAAGGGTCCTATTGCAGTTTCCCC
CATTTAATGGGTCATTAAAATATTCTTGGGAAGGACAAAGCTTTAGTT
AACTATGAGAAAAACAAGCAGAACCAGCCCTGGATTCTGTCTTCAAAG
ATTTTACCATGTTGGCAGGCCTGGTAGTCCAGAGCCCAAGAAAATATC
CCAGCCACAGATACCCTAGATGTAGACTAGCAGTGCTACAACCTCAAG
GTCAGAAGTATGTCACTAGACCAGAGCCAAAAATAGGTGCTATATCAT
TAAGAGAGTAAAAATGCAAACCACAGACAGGGTGACATTATTCACAAT
AAGCATATAACCCACAGGGGACTCCTATCTGAATATGCAAAGAACTCT
CACTAATCAATAAGAAAAGGCAAAGATTTAAACAGGCACTTCACAA
AAAAGTATATTCAAAAAATCAATAAACATTTGAAAAGATCCTCAATT
CACTAGTTATTAGGGAAAGGTGAAATAAAACCACAATGAGACACCCCC
ACGCCCCACCAGAACGGCTTAAAATCTAAAACATGTAATACCGAATG
TTTGCAAGGATGCGGAGAAACTGCCATTTTTGTACACTGCCAGTATGA
GGGTAAATCTGTACAACCAGGTTGGAAAACGCTGAGTAGAATGTACTC
TAGCTGGATTTGTGAATATCATATGATCCAGCAATTCTACTCCTAGAA
ATTTACCCAACAGAAATGTGTAAACATGTTCACCAAAAGACACACGCA
AGACAATTCATAGAGGCACTCACTATTCCTAACAGTCAAAAACTGGAA
ACTACCCAAATGTCCATCAGCAGAGAATGGCGATAAACAGTAGCATCT
TCACATAATGAAATGTTTCGACAGCAATGAAAAGTAGCTAGCTACAAC
TACAAACAATGTGATTGAACCTCACAAACATATACTAAGTAAAATTAT
CAGACACAAAGAGTGTATATACTGTATTTAGATACATGTGAAGTCTGA
AAACAGGCAAAACTATTCTGTTGTTAGAAGTCAGAATAGTTACTGCCC
TGCCGGGAAACAGAACTCAAGAGGGCTTAGTAGCTACTGGTAATGTTC
TGCTTCCTGAACTGCATGCTAGTGAGGCAGCTGTTATTTTGTGCAGTC
CTGTGTTACACTGGAGTTAAAAGTTCCCCAAAATCAGAAAGTGTTCA
GCAAGTGGAAGCAAGTACACTGCTGGACTTGGCTGGGAACTTAGGGGA
TCCCATAATTTGTCACAGGCACAAGCAAAGCCAGCTTTCTTGCCNTAA
GTAGCATCTCCCAGAGTCAGGATCCAGGAATGGTTTGGCAGGCAGGAT
GCAAGGCAGGATTCGGGAGTGGCTGAGAGTTTTCCCAGTGCCACCTGG
TCCCACCTCCCCTCTCCCACTTCTAATGAACGGGCAGTACAGCTTCTG
TTAGGAAAAGAGCCTGGGTCCCTAGGCGATGACTGTCACATCTAGGGA
GAGGGCGATGCACTGGGGTCCTCACCTACACCCCCCTTGGCTGTCTCA
CCACTCTGAATTATAAATGCCCGGACTTCCTCATCTCCCACCCACACA

FIG. 4A (2)

```
TCTTGTTAGAAGAAAAGAAACGAATCTCCCAGGGCTCCTTCTAACAAA
AGTGTTCATTCAGAGTAGCCCTGCTTGAGGGCCCCTGGCCTGGAGGAG
TGGGAGAGGCAGCCCTCCCCCTCCAGGAGAGTCATCTCCAGGGCTACC
CAGGACTGAGTAACTAGGTCACCAGAGTAACCAAAGAGGCAGGAGACA
AGGGCATTCAAGCATTGGGCCAGGAATGGAGGGTGATGTCCAGTTCAT
GTTCTTCTGGTTCCAGCATAGCACACGGTGCAAATGAACCATCATGCA
AGAAAACACAGCTAGTCTCCCTTCCTCCACCAGCAACCTTTGGTTACT
GATAATAATCAAATTCACTATTTTTTTTTTTTTAACTAAGGCTGAG
ATAATGTCAAAGGACCACAGGGAATAGGAAGGCCTAAACCAAGGCCTT
AAAGAATGAGAAGAAGATTCATTCAAAAAGCCTCCTAAGGGAGGAAG
ATGTTTTCCCTCCTTTACTTTTCTACAGTAATTTTTATTTTGGATAA
ATAAACCCTGATAAATGAGAACCCACGCTTTCCCAAGGCCAGGCTGTG
TTTTGGTGGGTGGTCCTCGTCAGCAGTTGGAGTAATCCAGAGTGATC
CCGGGCAAGTCGGAAGGGAGCAAGTCTGTGTTGAAGCCAAGAGGTATC
TTTCCCTACAGCTTCTCAAGAGAGGGGATCCCCGTGGGTAATTGTGAG
GCTGGAAACACCGAGAGGCTGACTCCCATGTTTATAGAGGTCATTGAT
GGGTTTGTGCATGGAAGGCAGGAGGAGACTGAGAGTGCTTTGTTATTG
TTATTTGGTTTATTTTTATTTTAAAAAACTGGATCAGCCGACTTTGA
ATACAGAAAATGAAAATGAGGAGATTTGCATAACAGCGCTTGGACGT
CTGAAGGGGCCCAGGGCCTAGCGGCTGGTGGGCACCTAGAAACACTT
CTGCCTGCAGATCGCGGAGGGTTAGCCACAGGAAGGGGTCGCCTAGGC
TGGCCACAGGGCCTTTGCTGTGACTGAAGGACCAGCCTTGGCGGCACC
TTCTTTCCCCTCTGCCCTGCACTCCGGCCCCGCCGGAGTCAGAGCTGA
CTTGCTGCAGGTTGGGGAGAGGACAGAGGCTAGGACGGTGGCGAAACC
TCACCTCGTCGCAGTCCGGAAGGTAAACTTGGACCCGGCAGGCACTTC
CTAAAGTCCAAGCTGCCCTCTCTGAAGAATAAACCTGATTTTCCTCCG
GACGCGGACAAAGGAGGATTCGCTCACAACTAGCCTGTAACAAAGATT
CCCTATTTTCGTGGTTAGGAAAAAAAAAAAAAAGGAAGCCCTCCGGGA
GAGACATGCGCCCTAATATTTCTCCCAGATGGGCCGGGTTCAAGCGCG
TTTGAGAGTTTGCTCTCCTACCAGCCTCGGGTTCTAGGCCCCCCGCAC
CCTCATCCTGGCTCCGCCCCTTCTCTCCACCCTCCCGGACCCCTAAA
GGGGCGGCGGGCCCAAGCCGAGGGCGCTGCGCCTGACCCCGAGCGGA
AGGGCCCCAGTCTAGGTCCTAATGCGGGTGGCGTCTCCTTTGACAGGC
GGCGTTTGGGGACAACAGCGGGGACGAGAGATAAGGTGACATACCAGA
GCAGATTGGTGCGCGCGCTGATACTCCTCTCCCGACAGGAAACGCGG
AGCTATTTAAAAGACCCATCGATTACTTTATCTTTCCTGGAAAGCTT
CTTGCGGAGAGACAAAAGATGTTCCCTGCCTAAAGACACAAGGCCACA
CAACGGAGGGTCTGCACAGGCGACGCACAATTCGGCGCGGGGAAAGCA
AAAACACACTGACGCTTAGAGTGCACAAACGTGTGTGTTCCCAGAGCA
GCTCCAGAGTGCGGCAGGGACGCTGGGGCGGCGAGGGGCACCCACAG
TATGGTCTTCTGTGCCCTTGGAAAGTTTTTTTTCACCGTATGCGCGTA
AAACACGCACACAGAGAAAGTGACTGTGCACTTAGGGCGCCTGTGT
GTACCCGTGTCGTTTAGCGAATTTAAAGCACATCAGGCCGGGCGCCA
TGGCTCACGCCTGTAATCCCAGCACTTTAGGAGGCCGAGGCGGGCCGA
TCACCTGAGGTCGGGAGTTCGACACCAGCCTGGCCAACATGGTGAAAC
```

FIG. 4A (3)

CCTGTCTCTACAAAAAATACAAAAATTAGCCGGGCATGGTGATGCGTG
CCTGTGATCCCAGCTACTCGGGAGGCTGAGGCAGGAGAATCGCTTGAA
CCCGGGAGGCGGAGGTTGCAGTGAGCCGAGATCACACCACTGCACTCC
AGCCTGGGCGACAAGAGCGAAATTCCGTCTAAAAAAATAAAATAAAAT
AAAATGATAATTAAGCCCATCAACTCACATTCAAAGCGGTTACTGGTG
GTTGTAATGTATCCATAGACACAGGTCTAAAATGTAAACGCTCCATTG
TGCTCCTTTTAAGGGCTTGAATGTCTGCAACTGTCATGTGTACACTTA
AAGTATGGGATGTGTCAACACGACCCTTTCTAGCGCGCTCGTTTCGTG
TCTGAATCCCCGCATTTCGCCAATTTGCTTGGAGCGCAGAACGCCCTC
CGCGAAAGGCGGCTGCTGATCCCGACTTTGCTCCGGTATCGCGCAGCT
TGTTGGCCTCCGGGTCCCCGTGCCATGCCCCGGGAGGCTCTCCACA
GACACCGCTTGCGCCGAATTATACGAGACTGAATGGGTTTTTTGGTG
TGTGTGTGCAACACAACAATTTGTCAGCTGCTGTTCACAATGCGCTCC
GCCGGGCGGTGGAAACTTGGCTGCGGTAACGCACAGCAGGTTGGAGGG
CACGACCCGGAAGGAAGGAAGAGGCGAGGAGGGAAAGGCGGCGACCCT
AGGCCCGCTGGCCAGCCGTTTCCAGCATCAATTCAGCACTGAGCCGGC
CGCAGCAGCACAGGGCTGGGGCTCCCGGAAGTTCGGCCAGCCGGGGT
TTGGGCCAGAGCCGCGGAGGCTGCCCGGTGGTAGGTGCGACTCTTCAC
CTCTCCGGGGAGCGGCGGCCGACGACCCAACCCACCCGCAAGCGCTGC
CGTCGGCCCGGCTGGTCCCCGCGCGGGCACAAAAACAGGCGGCAGTT
CGCCAGCTCTCTTTTCCCAAACCTGAACCGCCAAGCCGAAGGTTCTTC
CAAAGTCGCGGTTCCCCGGGCTTCACACCCGCCGGGCAGGCGCGAACC
AGCCCCAGGACAACCATTTTCCTCTTCACTGTATCTGAGTCGTTGTCC
ATCTGACTCGAATGTCACCTGATTTCCCAGCTGTGACCTCCAGCGAC
GGGACTCCGAGGAACTGATTCCAGCGTCTCGATTCTCTCCGCCTCTCC
GCCCGTTTTGGCTGAAGCGGTTTGCAGCCGTCGGGGCAGAAGGGGTGG
GATGTGGCAGCCACCAGCCCCAGCCAGAGAAGAAAAGAGGACGAAAT
TAACGCGAAAGGACACCGGAAGTCTGAAAGCGACTCCCTCGGATCCTC
GGAATCCGAGGCAAACCCTAACACTAGTTTGAAAGCGGATCATATCCA
CTAATCCAGGACAAATTCGGGTTGGGAAACATACTCCCCAGAGCCTAA
GAAAACTGACTTACAACAAAACAAAACTGACAAGGACAAAATGCAAAG
GAGTTTGTGAAACGTAATTGCTCTCAGAAAATATGTGTATATATATAC
ATCCTATAATATGTTTTAAATTTGCAAAAAAAAGTCTCTAAGAGGAT
ATATTTTAAAACCAGTGGCAGCTTGGGAGGGAGTGGGGATTAGCTGA
GAAGGGGAGAAGGAAGCATTTTGAGGTGACGTAAATGTTTTGTATC
TTGATTATGGTGGCTGTTATGGGGGTGCACATCCAAGTGTCAAGACTC
ATCGAACTGTACACTTTTGTTCTAGGTACATTAGACCTCAATAAAGTG
GATTTTAAACCTAAATAAGCCAGGTAACAGCTTTGCCTGGGTGGCTGG
GGGAGAGGCTTGGACACTTTACATTGATCTCCCTCTTAGGCATGTTC
GTTTGGTTTGGTTTGTTCTTATGATGTATTATTTATTCAAAAATAT
ATCATTAGCAGAGTGACTGATGTAAATGTAAAACCATTGTTAAGGAAA
CCAACAAAAGCGGGAACAAGAGACACTGGTGCATCCTGTTAGAGGGAT
AAGAATAAGCACTCGCTGTCCAAGCTCATAAAATATTTTGGGAATGAA
TGTCGTTCCGCTTTGTTTTTTGGTTTTTTTGCTCATGTGTTTAACAT
CAACGAGAAATGAGGACCCAAAACTTATCCAGTGGTTACGTGTGGTGT

FIG. 4A (4)

GTGTGGCTGTCATCTCCTTGGGACTGGCTACTGAAGGCCACAGGCGTG
GGAGGACCAAATGCTCCCTGGATGTTGAGTCCCAGCCGGTAAGCAGCA
CACAGTCCCGCTTGCAGCAAAGATGTGGTGGCCGGCTGCGCTGTGGGG
GAAGGCCAGGCCCGGACAGGAACCTCAGATCTCACCGGCGGATGAGAG
TGGTGCCCCCTGCAGCTGGAGTCCCTGCTGGCCTGAGAGCTCCAGCTG
TGCCACCGTTGGGCAGACCCCACACTTCAGGGAGCTGCCAGGATCAGT
GGCTACAAGAGTCCCCACCGTGTTTGGAGAAACTAGGTATGAAATATT
TCCATTTACACCCCTACCCCGGCCCCAGACAGGAAAGTCACTTCAACC
TTGTTAGGTCAGATTCCAGATCTGGTTCAGATGCAGGGCTATTTCAGA
GAGATTTTAGAGGCTGACTCTCAGGAGAGGGAAGGACAGTGGGCTGA
AGGCCAGGGGTCAGGAAATCTAGGAACTGCTAAACTCCTCTGCTGGCC
TGCGGGGAGCGCCCGGGTGGGGCTACCAAGGCCACAAGCCAGTTCCAT
CTTCCCACTTTGCCACCTTCTCACAGGGACCAGGCTCTGCATCCTCAG
TGACCACAAGACTTGGGCCTGCCCTCTAGTTTGTCTATACCTGCCCCC
TCCCTTGACTCATACTGTCCAAGACCCAAGACCAAACCACAAGTCAG
GAGAGATCTTGAGGGCAGCCAGTGCCACCAGGGTCCTGTTCCCAGGTA
CTACTAGACAAAGGCCACCCTTCCTCCCCTCTCTAGGGCTCCGCTG
ACCACCCTGCACAGTCTTCCTACACCAAGGGCTCCGGTGCCACCCCTT
CACAGAGAGTTCACTGCACCGCTGCTTCGGCTGCCTGTCTCAAACCAT
ACACACACCTTTGATTCTTAAACTCCAAGATTAGGATGGGCCCCAGAA
ATCTGCATTTTTAATATGTACCTCAGAGGATTCTGGCCTAGATATTTC
TACAGCCCCAAAAGTAACAAGGAACCTGTTCCAAAAAGTGTATTACGG
AAACTGTCATGTTTATTCTTGACTTGCCCCCCAATTATTCTTCCCCTG
AAGTTTTCATCACCAAAAAACCCCACATGTGAACCATATGTGTACATA
TGCCCATATTTAAAATACAAATTCTGCACCTGGTTTGCTATTTAAAGT
ATCTCAAAACATATCCATAAGAATACATATGAATGGAACTAATTCTTT
CTCATGGATATGGGATCTGTTCTATGGACAACATAATTTTTAACCAG
TCCTAGTATATATACACTGGTTTTTTACATGTTGATCTTAAAAAATAA
AAACGGNTGAAA (SEQ ID NO.: 4)

FIG. 4B (1)

```
CAATTTCTATTNAGTTCTATTAAAAGGGATTTTTTTNAACTCACTGGNAACCAGGAGGA
CTGNAAAGAAAAGTGAAATGGCTCTGGGACTTTCCTCTAAGGAGACCAGCATGGGTCGCC
CCAATTTTTATTTTGCACGTATTTGTCCGTTTTGCCCCATCTCCTCTCTCCTGAAACAC
CAAGACCTTTTTGGAAGCCAAGAGAAATCATTACCCGATTCACAAAGAGCATAGAGAGTG
TAACAGTCACTGATCTTGTTCAAATAGGGAGAGTTTTTTTTCCTTCCCTTTTTGTAACAC
CTGACCCACAGGACTGACAGTTCTAGGAAGCCCCCTTACCCGAAAATAGGAAATAAATCC
TTGCCACCTTGATTTGCAAGGGCAATGCTAATTTTTTTCTTTCTCCAGAGCTCTCAAAAA
AAAAAAAAAAAAAACCTTACTAAAAACAGGGATCCCGGATGTAGCCTCGATGTCCCCCAT
TAAACGGTAATATTTCAGGCGTCCGCTCACACTAATCTTTCAAACTGTCATCGCGAGCCG
CCTGGCCAGCAGATTCACTTAACAGCGCTCCCAGGACCCTCGTTCCGAGCTCTTTTCAGC
GAGACATTTAATTGAATCGGATGTGGCTCGTTTGCCAGACGTCACCGCCTCGGCGATAGG
CATCCTCTCCAACGACACCCCCCCCGCCCGCGCTCGAAAACAATCTTCAAAAGGCAAGG
GGGCCCCCCAAGTAGGTTAATTTACAACCATAACGGTAACGTGGCCAAAAGNCAGGCGAG
GAAGGGCCGCAAGGCCGCTGACATGCAAGCTCCGTCCAAGAAGAATTTGGGTTGGAGGTG
AAGAGGTGGGGGGACGAGGTTTCNTGGGCCTTGAACGCCCCACATTTAAAAAAGGCATCC
TCCACAGACTAGACTAACAATTCCAGACCCCAGTAGTCCCTGGCTCAGAAACTCGAGGC
GTGATTTCGGCGTGGCAGCCCAGGCCTGTTACTGACGGCTGGCGCCTAGAAGCCGGGGTC
AGGGCGTTGCGCGCCTCCTGGGCTGCCCTGCGGGGCTCACCTCTCTCCCCAGCATGGAGG
CCCCAGGTCCTGGGAGTGTGGCTTTGATGAGGGACAGGAAAAGTCCCAACATCAGGCCAA
TGCTTGACTTCACTTGCGTCGGCGTCTCAGACGGCACACTGTCGGGTTTGAGCACCCAAG
ATGTACGTTCTGGACAGACACTATTTTGTCCCCATACATGGAGCGTTTCCTCCGCACCTT
GGGCGCGCCTGCGGGAGCTGTGTCTTTAGGTAGTTTTTGGCCCTGCGCCGCCTTTATTCT
ACTCCAAGCGCTCTTTGCCAAACCCGCACTCCGCAAAGAGCCAAGCCCTCCACATCCCCA
TTCTCAGCAAGTCCACGCGTCCCGCCCAGCTTCCCGCCCGCGGTTCCCTGTACCAGCTAG
GGCCGTGAGAAGCCAACGCTTTTCCACTGACAAATCCTGTCATCCCCAGCTCTAGAAGGC
GTCCTTAACCTGGGCCCGCTCTGCCTGCCCGGACTCCTGAATTGTAAGCAAAATAAAACT
CCTCTCTGCAGTGTTCTGGGGAATGGAGAAGACCCCAAGCTTTCATCAGACCCTCCCAAG
GAGTGCGGGACCCAGAGAAATGAGGCCACCCGGGCAGGATCTGGCCATGTAGCTGGCGC
TCCTGAAACTCTGGCAGATTTGTCTGACTTCTGTGCCCTACTCTACTGACCCTGGGCTAA
AAATGATCATGATCACCCCACTTGCCCTGCCCTTCCCCCACGCGCCTGACCGAGCCGCAG
GGGTGCCCCACTGGAAGTCCGGCCCAGAGGCCTCAGAGAAATCCTGGCCTAGCTGGGCTC
AGAGGAGCCCCGCCTCCCTGAGAGCTAAACCTGGGCTAGGACCCTGAAACCTCGAGGTTG
GCAGAAGCCTGAGGGCCTTGCTGCCAGGCAGGGAGGGCACGGGAAGGAGGGAGGTGGGAT
CGATGGCCTCCAAACAGGGGAAACAAGGTGGCTGGTAGCTGGGGCACTCCACAAGACAGG
TGTNTCCTGGGAAGCTGAGCTTACCAGCTGGGATTCCTGATTTATTTCATTATTAAGGGG
AGAGGCATTTCCCCTGGGAGGGTACTGGCAGTGACTGATGCCCCTGGAGTTGTGCTGTG
CATAACACTACTGTAGGAGGCAGCAACTCCTACCCCACCTGGCCATCACTCACCTTGCCC
TTACTTTCGTTGATTCGCCCAGAAGCACCCAGAGCCTGCGGCATGATTGACCCTGTAGGC
CAAGCCAAACCAAACCCCCGAATTGTCCAGAATTTTCGCCCTGGTGTATCCCCAAAGCCC
AGCCCTGTCTTTNAGGGTTTTTTTCCTATTGAGATTTTCCCTCATCCCACCACCTTTAGT
AATAAAGCCTTCCTCAAACTAATTTCCTCCCCACCGCTTCCCACCCCATCCTTTTTTTTT
CCCATGCTGGTTTGGGTGCTGAGGAATATTTTTCAAACCCACACCCATCCAGCCCTGCC
CAGAGGCCTGACTTTGCATGCCTCTGGTAGGNTTTTCAGGGTTACATTAGGGAGCAAAAG
CAGGGTGCAGGGGCAAAAGGGGACCCTTCCAAATGGGTCGTGGCCCCTTTAAAAAAGCTG
GGCAGGGNTTTTTTTTTTTTTTTTTTTTTTTTTTTTTTTTGCCGTATGACTATA
```

FIG. 4B (2)

```
TTAGGTGACACGAAACTGCTCATCGCTCCTGTCATCGAGGCCCCTGGCCCAATGGCAGGC
TGAGTCCCCCTCCTCTGGCCTGGTCCCGCCTCTCCTGCCCCTTGTGCTCAGCGCTACCTG
CTGCCCGGACACATCCAGAGCTGGCCGACGGGTGCGCGGGCGGGCGGCGGCACCATGCAG
GGAAGCTGCCAGGGGCCGTGGGCAGCGCCGCTTTCTGCCGCCCACCTGGCGCTGTGAGAC
TGGCGCTGCCACCATGTTCCCCAGCCCTGCTCTCACGCCCACGCCCTTCTCAGTCAAAGA
CATCCTAAACCTGGAACAGCAGCAGCGCAGCCTGGCTGCCGCCGGAGAGCTCTCTGCCCG
CCTGGAGGCGACCCTGGCGCCCTCCTCCTGCATGCTGGCCGCCTTCAAGCCAGAGGCCTA
CGCTGGGCCCGAGGCGGCTGCGCCGGGCCTCCCAGAGCTGCGCGCAGAGCTGGGCCGCGC
GCCTTCACCGGCCAAGTGTGCGTCTGCCTTTCCGCCGCCCCGCCTTCTATCCACGTGC
CTACAGCGACCCCGACCCAGCCAAGGACCCTAGAGCCGAAAAGAAAGGTGAGGAGGAAAC
ACAGGCCCCCTTCTCCCCTCCTGGGTCGCTTTCGTCCCCAAGAAACTCAGGGCCAGGAGG
AGGACACACGCGCCCTTGGGCCGAGGGCTGGGCTGCGGCGGGGGGTTCAGAATGTAAGAT
GCCTGGTGTTGTCGCCAGGCTCCCGCGCCCCGCGTCCAATCGGAGGTTCAGAGGAAATGC
CGGATTGAAAGGATCCGAAAGCAAGAGACCAAAAAACTTTTCCCCCCGGCCTAACAAACC
CCCGGCGGTTTCCGCTCTGCTCCTGGTTCTGGTAGAATTTTAAAAATCGGTTTATGGTTA
AACAAAACAAAAAAACAGCCAAAACCCCGTTTTTTACCCCCCCCTTGGATTTTCAAACC
CTTTTTAAAATTTTTGAAAAAAAACCCCCAAACAAAATTAAATTTTTTCCCCCAAAAAAT
TTTTTTTTTTAACAAAAGGGGGGTGGAAAATTTTTTTTTCCCCCCCCCAAAAGGGGTT
TTTGTTTTTTTTTT--------TTTNTTTGGCAAAAATGAATTNTGGANCNAGGCCTTAT
TTNAAATGGATATTGGGNCCNCAGGATTTTGATTTCATTTATTTTTTAAGCAAACTTNC
CGGGCCGGCAAGGGGAAAGGTTCCCTCGTGGAAAAGTAGGAAATGCTGCGCTACCGCGGG
CACAAGGNAGTGGACGAGATGAGTGCGGGATCATCCCGCAGGCCATCCCAGGATCGGGGA
GGGAGGCCGGCCCCGCTGCAGAAAGGGGCTTCTGGGAGACCCCCAGCCCAAGGCAGGAG
CCCGGGCGATTCCCGGGAGGCCGCAGGCGCTGGGCGAAGCGCTGGGCGAAGGGCCGCTGC
CAGCCGGGAGAGAATTCATAGGTTTGTTGAGGAGCAGAGGCCTGGGAACAAATTCGGGCG
GGCACGGCGGCTAGAACTGATCGCTACCAATTCGAGGAAGCCAGCAAGGCAGGTTCCGAG
GCCGCCTGCCCACCCGCAGCTTCTTGGACACTGCGCAAACCCTGCTGCGGCCAGGCTGGA
GCCTCCGATCACCAAACCAACACTCCCTGGCCTTCTGTTTCTTGATTCCTTAATTTTGAG
ATAAGACCGTCCCTAGCAGTGAGGCCTCGGCCTCTGTTCATTTAACTTCTCAAACCAAAC
TAGCCCTAATTCAGTTCACCCCAGAGCATCACCTGGTTTTATTTTATTTTTTATTTTT
TTATTTATTTTTTTTTTTGCAGCCTGAAATTTAAGTCACCGTTTGTCTCCCTCACC
AGGGTGTGAACTGCCCCGAGGGCAGAGACCTCCCGTTTTGTTTTCCAGCGCCTTGAGCCA
GCTTGACTTTTTACAAATGCTGAGTGAGACGTGTCGGTGGCTCCCAGTGCACTTGGCAGA
GTGAGCCGCAGCCAGCTGGGCGCTCCAGGCAGGACACAGTGGCCTCCACGAGGATCCCTT
ACCATTACTGTGCGGCCGCGCTCCGTAGGTCAAGCCGCTCTTACCAAGCGTCTTTCTGCC
TTTCTGTTCCCCCTCAGAGCTGTGCGCGCTGCAGAAGGCGGTGGAGCTGGAGAAGACAGA
GGCGGACAACGCGGAGCGGCCCCGGGCGCGACGGCGGAGGAAGCCGCGCGTGCTCTTCTC
GCAGGCGCAGGTCTATGAGCTGGAGCGGCGCTTCAAGCAGCAGCGGTACCTGTCGGCCCC
CGAACGCGACCAGCTGGCCAGCGTGCTGAAACTCACGTCCACGCAGGTCAAGATCTGGTT
CCAGAACCGGCGCTACAAGTGCAAGCGGCAGCGGCAGGACCAGACTCTGGAGCTGGTGGG
GCTGCCCCCGCCGCCGCCGCCGCCTGCCCGCAGGATCGCGGTGCCAGTGCTGGTGCGCGA
TGGCAAGCCATGCCTAGGGGACTCGGCGCCCTACGCGCCTGCCTACGGCGTGGGCCTCAA
TCCCTACGGTTATAACGCCTACCCCGCCTATCCGGGTTACGGCGGCGCGGCCTGCAGCCC
TGGCTACAGCTGCACTGCCGCTTACCCCGCCGGGCCTTCCCCAGCGCAGCCGGCCACTGC
CGCCGCCAACAACAACTTCGTGAACTTCGGCGTCGGGGACTTGAATGCGGTTCAGAGCCC
```

FIG. 4B (3)

```
CGGGATTCCGCAGAGCAACTCGGGAGTGTCCACGCTGCATGGTATCCGAGCCTGGTAGGG
AAGGGACCCGCGTGGCGCGACCCTGACCGATCCCACCTCAACAGCTCCCTGACTCTCGTG
GGGAGAAGGGGCTCCCAACATGACCCTGAGTCCCCTGGATTTTGCATTCACTCCTGCGGA
GACCTAGGAACTTTTTCTGTCCCACGCGCGTTTGTTCTTGCGCACGGGAGAGTTTGTGGC
GGCGATTATGCAGCGTGCAATGAGTGATCCTGCAGCCTGGTGTCTTAGCTGTCCCCCCAG
GAGTGCCCTCCGAGAGTCCATGGGCACCCCGGTTGGAACTGGGACTGAGCTCGGGCACG
CAGGGCCTGAGATCTGGCCGCCCATTCCGCGAGCCAGGGCCGGGCGCCCGGGCCTTTGCT
ATCTCGCCGTCGCCCGCCCACGCACCCACCCGTATTTATGTTTTACCTATTGCTGTAAG
AAATGACGATCCCCTTCCCATTAAAGAGAGTGCGTTGACCCCGCACGTGTGCTTCTTTCA
GCTTGCGGCGCTTCAGAAGCAGGAGAGAGGTGGCCGCCCGGGACTGGTCTCAGATCTCAG
GCACAGGCATTCCCTGAGCAAATTGATAACATTGATACTAATAAAACCTAACCCTTGCTG
GAACCATACTGGTTCCGTGTCGGGCACTTTCTGAGATTGTCTCATATAATCCTCAATAAT
CCAAAAAAAAAAAAATCCTAAAGTTTAGAAGCTGAGGCCCGGAGAGGTTTAATGACTTAC
CTGCGAGCAAATAGCCAGTACTAGTCGAACTCTGGTTAAATTCAGGATGCCTCACTTCAG
AGACCGCCTTCCCTGTGCTCCCAAGCTCCCCTCCTTGAATCCTAATGTGTGCCAGGCACG
GTTCCAGGCACTGGGCATTAAATGGACAAGCAAAAGAACCTGGGCCCTCTGTAGCTGGAG
AGCACCGTGATCATCCCACTTAAAAGAACTCCTTAACCTGTTTCCAAGATGGNAAAAGCC
AAGAANCCAAAGCCCTTGGGNAAGCGTTCTCAAGGGTCCTCANATGCCCCAAATGCCACG
TCGGGGGCTCAACANCTNGCCCGTTGGAACTGAATGCCNANGGTGGGCCCCAAANAAGGN
TCCTGCGGGATGGNGCTCAACTCCAAGCTGTGGTGAAGGCCCATAAAATTCAAATGGGCC
AAGGGGAGCCCCCTAAAGCCCTAAACCTTCNGGGGGTCCNTTCCCTAAGGGCATTTAANT
TTACCAAAAGTTTGGNCAAANAATGTTTCCAATGGNCCNGATTTTATNGANGGGNAAAAC
TGGNGGGCAACCGAAATCCAGTTTAAACCCGGGTTGTTT (SEQ ID NO.: 5)
```

FIG. 5A

AGGCCCCCCG CACCCTCATC CTGGCTCCCG CCCCTTCTCT CCACCCTCCC
GGACCCCTAA AGGGGCGGCG GGGCCCAAGC CGAGGGCGCT GCGCCTGACC
CCGAGCGGAA GGGCCCCAGT CTAGGTCCTA ATGCGGGTGG CGTCTCCTTT
GACAGGCGGC GTTTGGGGAC AACAGCGGGG ACGAGAGATA AGGTGACATA
CCAGAGCAGA TTTGGTGCGC GCGCTGATAC TCCTCTCCCG ACAGGAAACG
CGGAGCTATT TAAAAGACCC TATCGATTAC TTTATCTTTC CTGGAAAGCT
TCTTGCGGAG AGACAAAAGA TGTTCCCTGC CTAAAGACAC AAGGCCACAC
AACGGAGGGT CTGCACAGGC GACGC    (SEQ ID NO.: 1)

TGCTCCTTT TAAGGGCTTG AATGTCTGCA ACTGTCATGT GTACACTTAA
AG (SEQ ID NO.: 2)

FIG. 5B

```
AGGCCCCCCG CACCCTCATC CTGGCTCCCG CCCCTTCTCT CCACCCTCCC
GGACCCCTAA AGGGGCGGCG GGGCCCAAGC CGAGGGCGCT GCGCCTGACC
CCGAGCGGAA GGGCCCCAGT CTAGGTCCTA ATGCGGGTGG CGTCTCCTTT
GACAGGCGGC GTTTGGGGAC AACAGCGGGG ACGAGAGATA AGGTGACATA
CCAGAGCAGA TTTGGTGCGC GCGCTGATAC TCCTCTCCCG ACAGGAAACG
CGGAGCTATT TAAAAGACCC TATCGATTAC TTTATCTTTC CTGGAAAGCT
TCTTGCGGAG AGACAAAAGA TGTTCCCTGC CTAAAGACAC AAGGCCACAC
AACGGAGGGT CTGCACAGGC GACGCACAAT TCGGCGCGGG GAAAGCAAAA
ACACACTGAC GCTTAGAGTG CACAAACGTG TGTGTTCCCA GAGCAGCTCC
AGAGTGCGGC AGGGACGCTG GGGGCGGCGA GGGGCACCCA CAGTATGGTC
TTCTGTGCCC TTGGAAAGTT TTTTTCACC GTATGCGCGT AAAACACGCA
CACACAGAGA AAGTGACTGT GCACTTAGGG CGCCTGTGTG TACCCGTGTC
GTTTTAGCGA ATTTAAAGCA CATCAGGCCG GGCGCCATGG CTCACGCCTG
TAATCCCAGC ACTTTAGGAG GCCGAGGCGG GCCGATCACC TGAGGTCGGG
AGTTCGACAC CAGCCTGGCC AACATGGTGA AACCCTGTCT CTACAAAAAA
TACAAAAATT AGCCGGGCAT GGTGATGCGT GCCTGTGATC CCAGCTACTC
GGGAGGCTGA GGCAGGAGAA TCGCTTGAAC CCGGGAGGCG GAGGTTGCAG
TGAGCCGAGA TCACCACT GCACTCCAGC CTGGGCGACA AGAGCGAAAT
TCCGTCTAAA AAAATAAAAT AAAATAAAAT GATAATTAAG CCCATCAACT
CACATTCAAA GCGGTTACTG GTGGTTGTAA TGTATCCATA GACACAGGTC
TAAAATGTAA ACGCTCCATT GTGCTCCTTT TAAGGGCTTG AATGTCTGCA
ACTGTCATGT GTACACTTAA AG (SEQ ID NO.: 3)
```

FIG. 5C

```
AGAGAAATCA TTACCCGATT CACAAAGAGC ATAGAGAGTG TAACAGTCAC
TGATCTTGTT CAAATAGGGA GAGTTTTTTT TCCTTCCCTT TTTGTAACAC
CTGACCCACA GGACTGACAG TTCTAGGAAG CCCCCTTACC CGAAAATAGG
AAATAAATCC TTGCCACCTT GATTTGCAAG GGCAATGCTA ATTTTTTTCT
TTCTCCAGAG CTCTCAAAAA AAAAAAAAAA AAAACCTTAC TAAAAACAGG
GATCCCGGAT GTAGCCTCGA TGTCCCCCAT TAAACGGTAA TATTTCAGGC
GTCCGCTCAC ACTAATCTTT CAAACTGTCA TCGCGAGCCG CCTGGCCAGC
AGATTCACTT AACAGCGCTC CCAGGACCCT CGTTCCGAGC TCTTTTCAGC
GAGACATTTA ATTGAATCGG ATGTGGCTCG TTTGCCAGAC GTCACCGCCT
CGGCGATAGG CATCCTCTCC AACGACAC (SEQ ID NO.: 6)
```

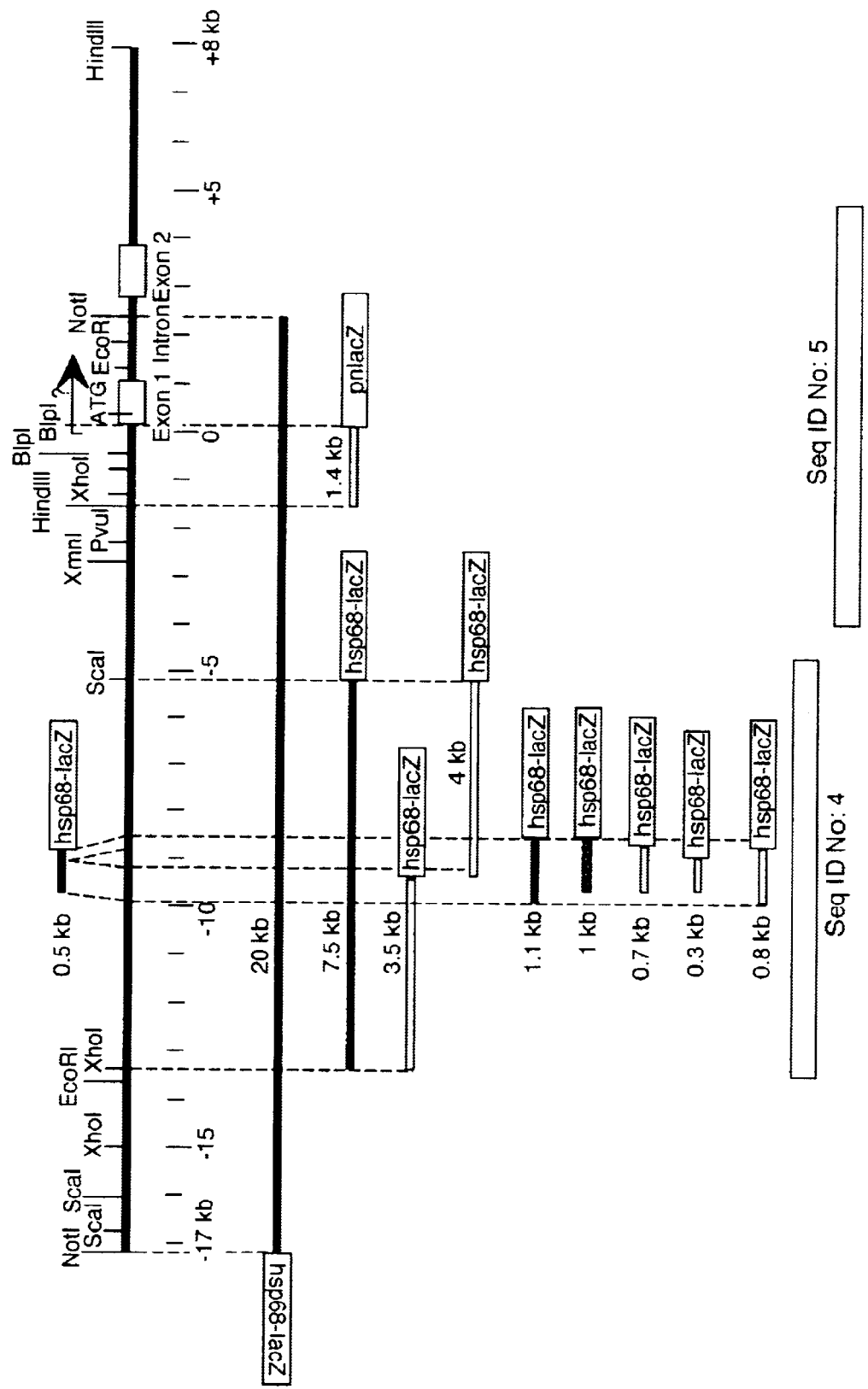
FIG. 6 Transgenic Constructs of the Human Csx/Nkx2-5 Enhancer

FIG. 7  Transgenic Analysis of the Human Csx Enhancer Sequence

| Constructs | | # of Transgenes | Enhancer positives (Cardiac : Ectopic)[1] |
|---|---|---|---|
| 20 kb | | 8 | 4 : 0 |
| 7.5 kb | | 8 | 6 : 1 |
| | promoter-proximal 4 kb | 7 | 0 : 1 |
| | promoter-distal 3.5 kb | 6 | 0 : 0 |
| 1.1 kb | | 8 | 3 : 1 |
| 1.0 kb | | 10 | 1 : 2 |
| 0.7 kb | | 8 | 0 : 3 |
| 0.3 kb | | 11 | 0 : 6 |
| 0.8 kb | | 6 | 0 : 1 |
| 0.5 kb | | 2 | 2 : 0 |

1. Each embryo was classified into either 'cardiac' or 'ectopic' judged upon the extent of similar to the endogenous Csx expression pattern.

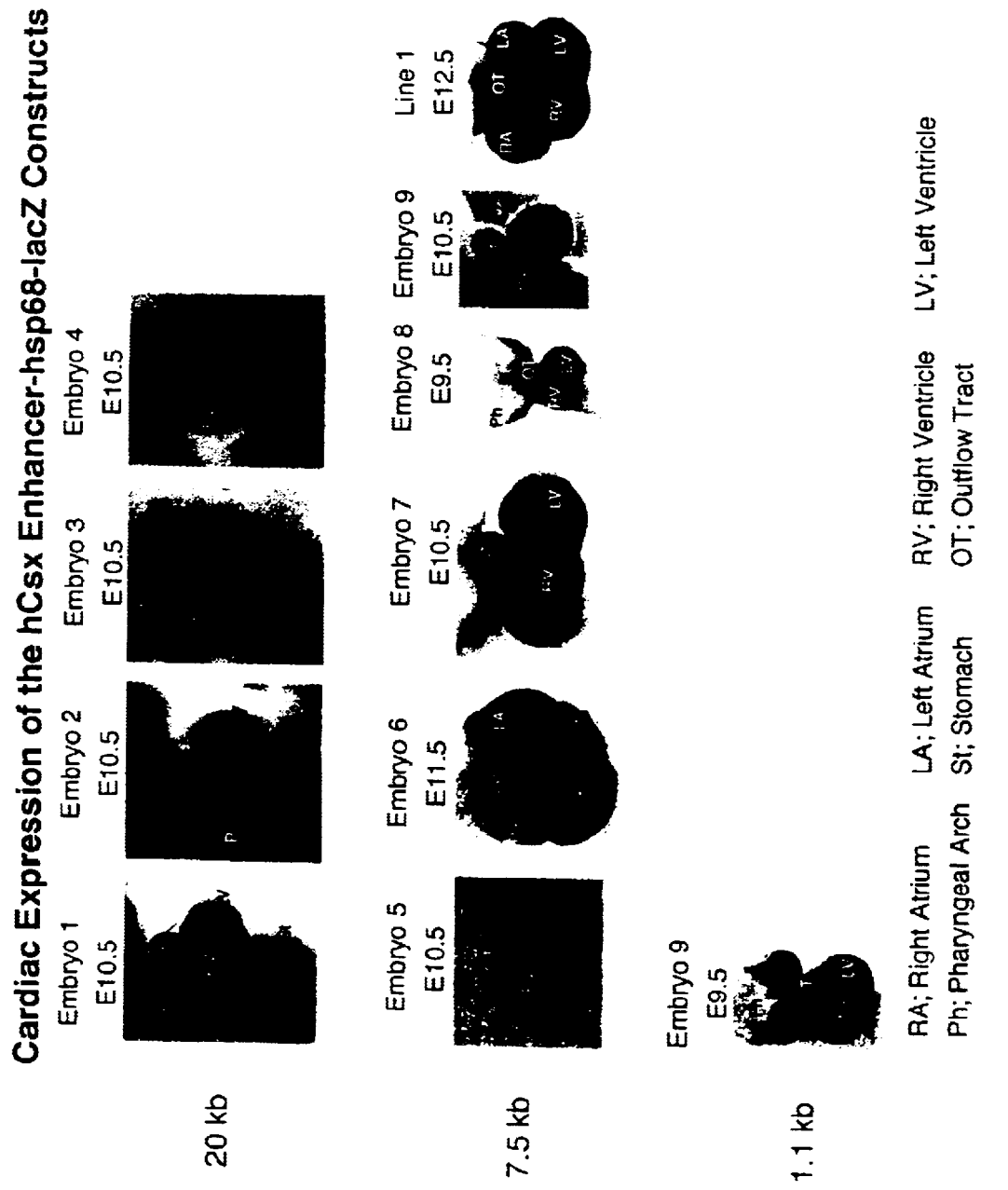

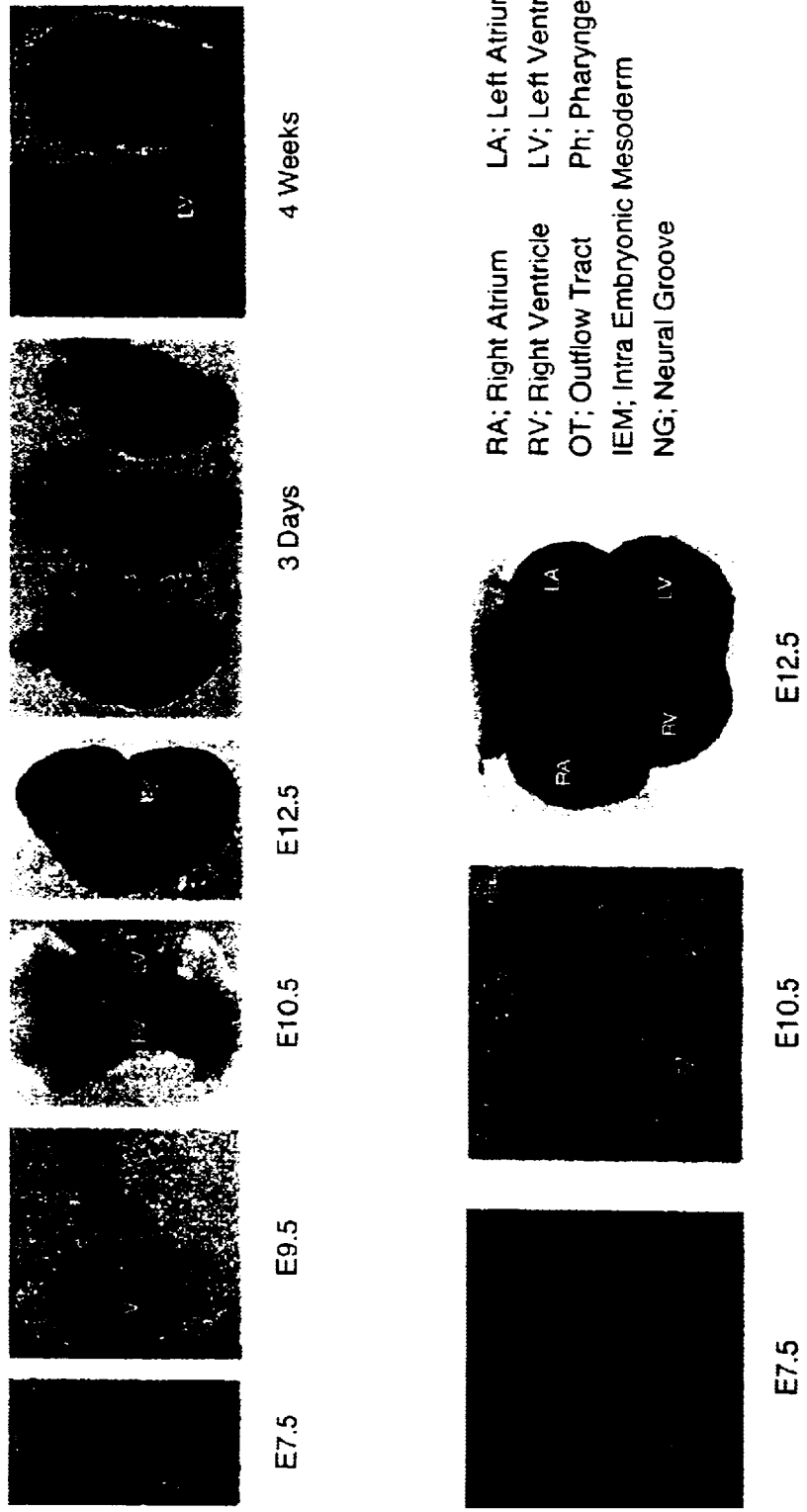
FIG. 9 Cardiac Expression of the 7.5 kb hCsx Enhancer-hsp68-lacZ Construct
RA; Right Atrium  LA; Left Atrium
RV; Right Ventricle  LV; Left Ventricle
OT; Outflow Tract  Ph; Pharyngeal Arch
IEM; Intra Embryonic Mesoderm
NG; Neural Groove

CARDIAC-CELL SPECIFIC ENHANCER ELEMENTS AND USES THEREOF

CROSS-REFERENCE OF RELATED APPLICATIONS

This application claims benefit from U.S. Provisional Application No. 60/176,419, filed Jan. 14, 2000 (now pending), hereby incorporated by reference.

BACKGROUND OF THE INVENTION

The invention relates to reagents and methods for expressing gene products in cardiac cells or precursors to cardiac cells in vitro and in vivo.

Adult mammalian cardiomyocytes do not de-differentiate or re-enter the cell cycle. After being placed into cell culture, neonatal cardiomyocytes soon lose their ability to proliferate. Several cell lines, including P19 teratocarcinoma cells, embryonic stem (ES) cells, AT-1, H9c2, QCE-6, or 10T1/2 cells, have some molecular characteristics of cardiomyocytes. These cells are very difficult to manipulate, however, or are lacking important characteristics of cardiomyocytes. Because of these reasons, cultured neonatal cardiomyocytes from rats or mice are often used in in vitro systems, even though these cells are difficult to transfect (usually less than 0.1% transfection rate) and require long preparation procedures.

Recently, it has been demonstrated that immortalized cardiac myogenic (CMG) cells can be differentiated from mouse bone marrow stromal cells. This is evidence of the generation of cardiomyocytes from a tissue of extra-cardiac origin.

The possibility of bone marrow being an in vivo source of circulating cardiomyocyte progenitors has been previously suggested. A distribution of transplanted bone marrow-derived cells in a dystrophic mouse heart has been observed. Although the molecular characteristics of these cells were not identified, their location in the heart tissue indicated these cells were cardiomyocytes. Taken together, it appears that bone marrow stromal cells are an extra-cardiac source of cardiomyocytes in vivo, and in vitro induction of beating cardiomyocytes from a heterogeneous population of bone marrow cells is possible by the introduction of inductive agents such as 5-azacytidine.

The molecular mechanisms which guide development of cardiac cells (and the heart in general) in vertebrates have been the subject of intense investigation (Fishman and Chien, Cell 91: 153–156, 1997; Olson and Srivastava, Science 272: 671–676, 1996). In most vertebrates, the heart tissue initially develops as a crescent shaped mesodermal structure located anteriorly and laterally. This precardiac mesoderm is brought ventrally and caudally, by folding of the embryo, to a form a single midline heart tube with the inflow region located most rostrally. This heart tube undergoes looping, bringing the inflow, ventricular, and outflow regions of the heart into the alignment seen in the mature heart. Later, chamber septation occurs, valves develop in the atrioventricular (AV) junction as well as in the outflow tract, and the outflow tract itself is divided into two great vessels. Additional refinements occur with the development of the coronary arteries and the cardiac conduction system.

Heart development is governed by complex signals including inductive and positional signals from adjacent structures, as well as signals from a number of transcription factors (Fishman and Chien, Cell 91: 153–156, 1997; Lyons, Curr. Opin. Genet. Dev. 6: 454–460, 1996; Mohun and Sparrow, Curr. Opin. Genet. Dev. 7: 628–633, 1997; Olson and Srivastava, Science 272: 671–676, 1996). Since transcriptional factors have the ability to activate multiple genes, they are generally considered important regulators of organ development. A number of cardiac transcription factors have been identified that have important influences on the early stages of specification and differentiation of the cardiac mesoderm (Tanaka et al., Dev. Genet. 22: 239–249, 1998). Csx/Nkx2.5 (Komuro and Izumo, Proc. Natl. Acad. Sci. USA 90: 8145–8149, 1993; Lints et al., Development 119: 419–431, 1993), MEF-2C (Edmondson et al., Development 120: 1251–1263, 1994), GATA4 (Heikinheimo et al., Dev. Biol. 164: 361–373, 1994; Kelley et al., Development 118: 817–827, 1993) and dHAND and eHAND are members of four different classes of transcriptional factors all expressed in the heart at early stages of development. Targeted disruption of any one of these genes yields severe cardiac and extracardiac phenotypes, and results in death of the embryo between E9.5 and E10.5 of development.

The mouse Csx/Nkx2.5 gene is first expressed in the cardiac progenitor cells at embryonic day 7.5 (E7.5), and during this stage is detected principally in the heart and tongue (and, to a lesser extent, in spleen, stomach, liver, and larynx). The extra-cardiac expression of Csx/Nkx2.5 is markedly reduced after birth, however, and in the adult, the expression is confined to the heart. Mice in which the Csx/Nkx.2-5 gene has been deleted have no functional heart, causing an embryonic lethality by E9.5–11.5.

Most tissue-specific gene expression is controlled by enhancer and repressor sequences at the transcriptional level. Generally, to confer tightly-regulated expression, enhancers adopt complex regulatory mechanisms that require the collaboration of multiple transcription factors. The binding sites for these transcription factors may be many kilobases (kb) from the gene promoter and dispersed relative to each other.

It is desirable to be able to express genes in a cardiac cell-specific manner. This would be useful, for example, for the targeted expression of genes encoding therapeutic proteins for the treatment of damaged heart tissue. Moreover, to maximize the utility of stem cell-derived cardiomyocytes, for example, in the treatment of damaged heart tissue in humans and other animals, it is desirable to be able to rapidly purify cardiac cells from a potentially heterogenous cell population.

Accordingly, there is a need for the development of reagents and methods for achieving cardiac cell-specific gene expression. The present invention provides these reagents and methods.

SUMMARY OF THE INVENTION

In a first aspect, the invention features a substantially purified nucleic acid molecule comprising an enhancer element having: (a) 100% identity to 40 contiguous nucleotides of the nucleic acid molecule shown in SEQ ID NO.: 1 or SEQ ID NO.: 3; (b) at least 91% identity to 50 contiguous nucleotides of the nucleic acid molecule shown in SEQ ID NO.: 2; (c) at least 97% identity to 60 contiguous nucleotides of the nucleic acid molecule shown in SEQ ID NO.: 1 or SEQ ID NO.: 3; or (d) at least 95% identity to 70 contiguous nucleotides of the nucleic acid molecule shown in SEQ ID NO.: 1 or SEQ ID NO.: 3.

In a second related aspect, the invention features a substantially purified nucleic acid molecule comprising a cardiac-specific enhancer element derived from a human, wherein the enhancer element has at least 60% identity to 50 contiguous nucleotides of the nucleic acid molecule shown in SEQ ID NO.: 1, SEQ ID NO.: 2, or SEQ ID NO.: 3. Preferably, the element has at least 70% identity to 50 contiguous nucleotides of the nucleic acid molecule shown in SEQ ID NO.: 1, SEQ ID NO.: 2, or SEQ ID NO.: 3. More preferably, the identity is at least 80%, and most preferably, the identity is at least 90%, when compared to 50 contiguous nucleotides of the nucleic acid molecule shown in SEQ ID NO.: 1, SEQ ID NO.: 2, or SEQ ID NO.: 3.

Preferably, when expressed in vivo, the enhancer element is active in all four cardiac chambers. The enhancer element of the first or second aspect may be naturally occurring, or it may be non-naturally occurring.

Preferably, the enhancer element of the first or second aspect includes a binding site selected from the group consisting of Mef2, dHAND, GATA, TGF-β, CarG, E-box, and Csx/Nkx2.5 binding sites. More preferably, the enhancer element includes at least two binding sites selected from this group. The enhancer element preferably also includes an Sp-1 binding site.

In a third aspect, the invention also features a substantially purified non-naturally occurring nucleic acid molecule that includes at least three transcription factor binding sites selected from Mef2, dHAND, GATA, TGF-β, CarG, E-box, and Csx/Nkx2.5 binding sites. More preferably, the nucleic acid molecule includes four transcription factor binding sites, and most preferably includes five transcription factor binding sites selected from the aforementioned group. Preferably, the nucleic acid molecule, when operably linked to a promoter, increases activity of the promoter by at least two-fold in a cardiac cell-specific manner.

In a fourth aspect, the invention features a substantially purified nucleic acid molecule comprising an enhancer element having: (a) 100% identity to 50 contiguous nucleotides of the nucleic acid molecule shown in SEQ ID NO.: 6; (b) at least 97% identity to 60 contiguous nucleotides of the nucleic acid molecule shown in SEQ ID NO.: 6; (c) at least 93% identity to 70 contiguous nucleotides of the nucleic acid molecule shown in SEQ ID NO.: 6; or (d) at least 90% identity to 100 contiguous nucleotides of the nucleic acid molecule shown in SEQ ID NO.: 6.

In a fifth aspect, the invention features a substantially purified nucleic acid molecule that includes a cardiac-specific enhancer element derived from a human, wherein the enhancer has at least 45% identity to 50 contiguous nucleotides of the nucleic acid molecule shown in SEQ ID NO.: 6. Preferably, the element has at least at least 50% identity to 50 contiguous nucleotides of the nucleic acid molecule shown in SEQ ID NO.: 6, more preferably, the element has at least 60% identity to 50 contiguous nucleotides of the nucleic acid molecule shown in SEQ ID NO.: 6, and most preferably, the element has at least 75% identity or even 90% identity to 50 contiguous nucleotides of the nucleic acid molecule shown in SEQ ID NO.: 6. The element may be naturally occurring or non-naturally occurring.

In a fifth aspect, the invention features a substantially purified nucleic acid molecule comprising 50 contiguous nucleotides that have a sequence that is that at least 90% identical to 50 contiguous nucleotides of the nucleic acid molecule of SEQ ID NO.: 4 or SEQ ID NO.: 5.

In a sixth aspect, the invention features a DNA vector that includes the nucleic acid molecule of the first, second, third, fourth, or fifth aspects. The DNA vector can also have a promoter operably linked to a gene of interest. The gene of interest is preferably a cardiogenic gene (e.g., a gene encoding BMP2, BMP4, GATA4, dHAND, eHAND, MEF2C, IRX4, SRF, or Csx/Nkx2.5), a reporter gene (e.g., a gene encoding GFP, β-gal, alkaline phosphatase, chloramphenicol acetyl transferase, or luciferase), a gene encoding a selectable marker (e.g., a gene that provides resistance to neomycin, kanamycin, or hygromycin), or a gene encoding a therapeutic protein (e.g., a growth factor, a cytokine, an anti-apoptotic factor, a pro-apoptotic factor, or a protein that improves cardiac function or repair).

In a seventh aspect, the invention features a method for inducing a cell to become a cardiac cell. The method includes (a) introducing into the cell or ancestor thereof a DNA vector that includes (i) the nucleic acid of the first, second, third, fourth, or fifth aspect; (ii) a promoter; and (iii) a cardiogenic gene operably linked to the promoter; and (b) placing the cell under conditions that result in expression of the cardiogenic gene operably linked to the promoter. Preferably, expression of the cardiogenic gene further enhances expression of cardiogenic genes by binding to cardiac-specific enhancer elements.

In an eighth aspect, the invention feature a method for specifically expressing a gene in cardiac cells, said method comprising introducing into the cell or ancestor thereof a DNA vector that includes (i) the nucleic acid of the first, second, third, fourth, or fifth aspect; (ii) a promoter; and (iii) the gene operably linked to the promoter. Preferably, the nucleic acid allows expression of the gene in a cardiac cell and does not express said gene in at least one cell that is not a cardiac cell.

In a ninth aspect, the invention features a method for determining the efficacy of a method of inducing target cells to produce or become cardiac cells, the method including: (a) introducing into at least one target cell (or an ancestor of the target cell) a DNA vector that includes (i) the nucleic acid of the first, second, third, fourth, or fifth aspect; (ii) a promoter; and (iii) a reporter gene operably linked to the promoter; (b) performing a method for potentially inducing the target cells to produce or become cardiac cells; and (c) determining the number or percentage of cells that are reporter gene-positive, wherein a higher number or percentage indicates a higher efficacy of the method of inducing stem cells to produce or become cardiac cells. Preferably, the target cells are stem cells such as bone marrow stem cells or embryonic stem cells.

In a tenth aspect, the invention features a method for determining the efficacy of a method of inducing target cells to produce or become cardiac cells, the method including: (a) introducing into at least one target cell (or an ancestor of the target cell) a DNA vector that includes (i) the nucleic acid of the first, second, third, fourth, or fifth aspect; (ii) a promoter; and (iii) a gene, encoding a selectable marker, operably linked to the promoter; (b) performing a method for potentially inducing the target cells to produce or become cardiac cells;(c) performing a drug selection, wherein cells expressing said gene encoding the selectable marker are capable of surviving in the presence of the drug and cells not expressing the gene encoding the selectable marker are not capable of surviving in the presence of the drug; and (d) determining the survival of cells following drug selection, wherein a higher cell survival indicates a higher efficacy of the method of inducing stem cells to produce or become cardiac cells. In this method, step (b) can be performed before or after step (c). Preferably, the target cells are stem cells such as bone marrow stem cells or embryonic stem cells.

In an eleventh aspect, the invention features a method of identifying a cardiac cell, including (a) introducing into the cell (or an ancestor of the cell) a DNA vector that includes (i) the nucleic acid of claim the first, second, third, fourth, or fifth aspect; (ii) a promoter; and (iii) a reporter gene operably linked to the promoter, whereby the cell expresses the reporter gene if the cell is a cardiac cell; (b) allowing sufficient time for the reporter gene to be expressed in cardiac cells; and (c) identifying the cardiac cells by the presence of the reporter gene. Preferably, the method is performed in vitro.

In a twelfth related aspect, the invention features a method of substantially purifying a cardiac cell from a heterogeneous population of cells, including: (a) introducing into at least a subset of cells in the population (or ancestors of these cells) a DNA vector that includes (i) the nucleic acid of the first, second, third, fourth, or fifth aspect; (ii) a promoter; and (iii) a reporter gene operably linked to the promoter, whereby a cell expresses the reporter gene if the cell is a cardiac cell; (b) determining whether a cell in the heterogeneous population is expressing the reporter gene; and (c) if the cell is expressing the reporter gene, purifying the cell from the heterogeneous population.

In a thirteenth aspect, the invention features a method of expressing a gene encoding a therapeutic protein in a cardiac cell. The method includes introducing to the cell (or an ancestor of the cell) a DNA vector that includes (i) the nucleic acid of the first, second, third, fourth, or fifth aspect; (ii) a promoter; and (iii) a gene encoding a therapeutic protein operably linked to the promoter such that the gene is expressed in cardiac cells. The cell may be a cardiac cell, or it may be a cell that is capable of differentiating as a cardiac cell. The method may be performed in vivo or in vitro. If the method is performed in vitro, the cell (or a descendent of the cell) can be grafted into a patient.

In all of the foregoing aspects of the invention, an enhancer element is defined as a nucleic acid sequence that when present, (i) increases in a cardiac cell expression of a gene to which it is operably linked by at least 25%, (ii) allows for gene expression in the heart tube prior to looping, (iii) allows for gene expression in all four heart chambers; or (iv) increases cardiac expression 100% more than it increases extracardiac expression. Preferably, in (i), the expression is increased by at least 50%, more preferably by 100%, and most preferably by 200%.

As used herein, by "nucleic acid" is meant either DNA or RNA. A "nucleic acid molecule" may be a single-stranded or double-stranded polymer of deoxyribonucleotide or ribonucleotide bases. Unless otherwise specified, the left hand direction of the sequence of a single-stranded nucleic acid molecule is the 5' end, and the left hand direction of double-stranded nucleic molecule is referred to as the 5' direction.

By "promoter" is meant a region of nucleic acid, upstream from a translational start codon, which is involved in recognition and binding of RNA polymerase and other proteins to initiate transcription. A "human promoter" is a promoter capable of initiating transcription in a human cell, and may or may not be derived from a human cell. A "Csx/Nkx2.5 promoter" is one derived from the promoter region of a Csx/Nkx2.5 gene and that, when operably linked to a heterologous nucleic acid molecule, is capable of initiating transcription of that molecule (when present in a transcription medium capable of supporting transcription) in a cardiac cell.

By "enhancer element" is meant a nucleic acid sequence that, when positioned proximate to a promoter and present in a transcription medium capable of supporting transcription, confers increased transcription activity relative to the transcription activity resulting from the promoter in the absence of the enhancer domain.

By "operably linked" is meant that two or more nucleic acid molecules (e.g., a nucleic acid molecule to be transcribed, a promoter, and an enhancer element) are connected in such a way as to permit transcription of the nucleic acid molecule in a suitable transcription medium.

By "derived from" is meant that a the nucleic acid molecule was either made or designed from a second nucleic acid molecule, the derivative retaining important functional features of the nucleic acid molecule from which it was made or designed.

By "expression construct" is meant a nucleic acid molecule that is capable of directing transcription. An expression construct of the present invention includes, at the least, a cardiac-specific enhancer element and a promoter. Additional elements, such as a transcription termination signal, may also be included, as described herein.

By "vector" or "expression vector" is meant an expression system, a nucleic acid-based vehicle, a nucleic acid molecule adapted for nucleic acid delivery, or an autonomous self-replicating circular DNA (e.g., a plasmid). When a vector is maintained in a host cell, the vector can either be stably replicated by the cells during mitosis as an autonomous structure, incorporated within the genome of the host cell, or maintained in the host cell's nucleus or cytoplasm.

By "cardiac cell" is meant a differentiated cardiac cell (e.g., a cardiomyocyte) or a cell committed to producing or differentiating as a cardiac cell (e.g., a cardiomyoblast or a cardiomyogenic cell).

By "cardiac-specific enhancer element" is meant an element, operably linked to a promoter, that directs gene expression in a cardiac cell and does not direct gene expression in all tissues or all cell types. Cardiac-specific enhancers of the present invention may be naturally occurring or non-naturally occurring. One skilled in the art will recognize that the synthesis of non-naturally occurring enhancers can be performed using standard oligonucleotide synthesis techniques.

By "plasmid" is meant an autonomous DNA molecule capable of replication in a cell, and includes both plasmids designed for expression and plasmids designed for nucleic acid replication.

By "heterologous" is meant that the nucleic acid molecule originates from a foreign source or, if from the same source, is modified from its original form. Thus, a "heterologous promoter" is a promoter not normally associated with the duplicated enhancer domain of the present invention. Similarly, a heterologous nucleic acid molecule that is modified from its original form or is from a source different from the source from which the promoter to which it is operably linked was derived.

By "substantially pure nucleic acid" is meant nucleic acid that is free of the genes which, in the naturally-occurring genome of the organism from which the nucleic acid of the invention is derived, flank the nucleic acid. The term therefore includes, for example, a recombinant nucleic acid which is incorporated into a vector; into an autonomously replicating plasmid or virus; or into the genomic nucleic acid of a prokaryote or a eukaryote cell; or which exists as a separate molecule (e.g., a cDNA or a genomic or cDNA fragment produced by PCR or restriction endonuclease digestion) independent of other sequences. It also include, a recombinant nucleic acid which is part of a hybrid gene encoding additional polypeptide sequence.

By "transgene" is meant any piece of a nucleic acid molecule (for example, DNA) which is inserted by artifice into a cell either transiently or permanently, and becomes part of the organism if integrated into the genome or maintained extrachromosomally. Such a transgene may include a gene which is partly or entirely heterologous (i.e., foreign) to the transgenic organism, or may represent a gene homologous to an endogenous gene of the organism.

By "transgenic cell" is meant a cell containing a transgene. For example, a stem cell transformed with a vector containing the expression vector of the present invention operably linked to a heterologous nucleic acid molecule can be used to produce a population of cells having altered phenotypic characteristics.

Other features and advantages of the invention will be apparent from the following description of the preferred embodiments thereof.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

FIG. 4A shows the nucleotide sequence for SEQ ID NO.: 4,~7.5 kb of hCsx/Nkx2.5 genomic sequence, the genomic location of which is shown on FIG. 6.

FIG. 4B shows the nucleotide sequence for SEQ ID NO.: 5,~6.8 kb of hCsx/Nkx2.5 genomic sequence, the genomic location of which is shown on FIG. 6.

FIG. 5A shows the nucleotide sequence of hCsx/Nkx2.5 homology domains A1 (SEQ ID NO.: 1) and A2 (SEQ ID NO.: 2).

FIG. 5B shows the nucleotide sequence of hCsx/Nkx2.5 homology domains A1 and A2 and the intervening sequence that has no counterpart in the mCsx/Nkx2.5.

FIG. 5C shows the nucleotide sequence of hCsx/Nkx2.5 homology domains B (SEQ ID NO.: 6).

FIG. 6 is a schematic illustration showing the transgenic constructs of the hCsx/Nkx2.5 enhancer elements that were tested for cardiac-specific expression. The locations of SEQ ID NO.: 4 and SEQ ID NO.: 5 are also shown.

FIG. 7 is a table summarizing the transgenic analysis of the hCsx/Nkx2.5 enhancer elements. The constructs correspond to those shown in FIG. 6.

FIG. 8 is a series of photographs showing transgene expression in mice that resulted from the indicated enhancer-hsp68-lacZ constructs.

FIG. 9 is a series of photographs showing transgene expression in mice that resulted from the 7.5 kb enhancer-hsp68-lacZ constructs.

DETAILED DESCRIPTION OF THE INVENTION

Figure 1:
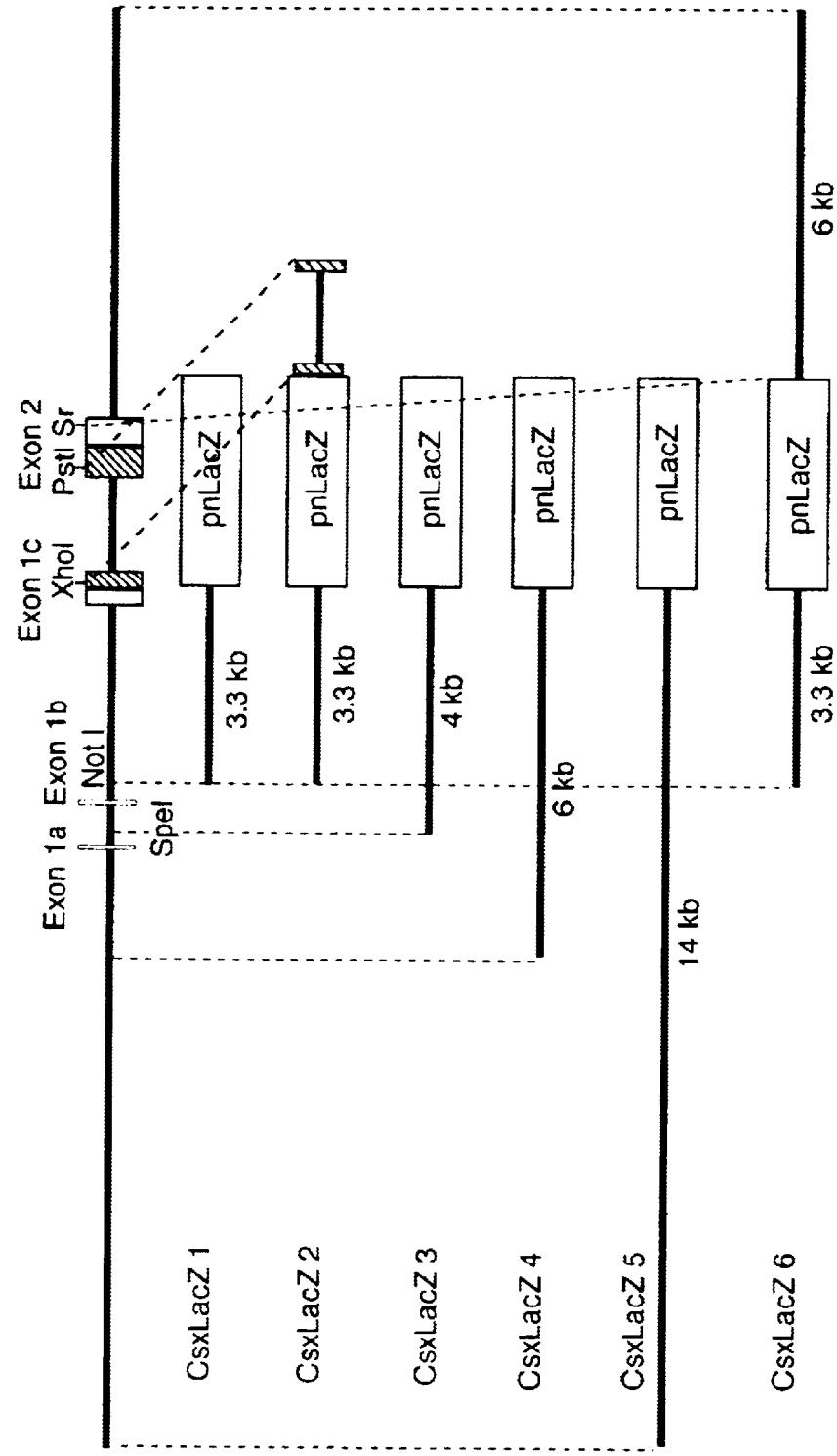
FIG. 1 is a schematic illustration showing the structure of the mouse Csx/Nkx2.5 (mCsx/Nkx2.5) locus constructs utilized for transgenic experiments. Open boxes and shaded boxes represent untranslated sequences and coding sequence, respectively. Various subfragments of these two λ phage clones were utilized for construction of transgenes (CsxlacZ-1 through CsxlacZ-6).

We have cloned cardiac enhancers from hCsx/Nkx2.5 and mCsx/Nkx2.5 that, when used to drive transgene expression in mice, recapitulate expression patterns of the endogenous mCsx/Nkx2.5. One of the hCsx/Nkx2.5 enhancer constructs, 7.5 kb-hsp-lacZ, constructed by operably linking 7.5 kb of genomic region from hCsx/Nkx2.5 (SEQ ID NO.: 4) to an hsp68 promoter-lacZ cassette, is active as early as E7.5, the earliest time point of cardiac development, and recapitulates the expression pattern of endogenous mCsx/Nkx2.5 at E9.5, E10.5, and E12.5. Thus, when the four chambers of the heart are formed at E12.5, the enhancer is active in all four chambers. Among the mammalian cardiac enhancers known so far, this 7.5 kb enhancer is the earliest enhancer that is active in all four chambers. Moreover, this enhancer displays no ectopic expression.

Within this 7.5 kb fragment, we have further isolated two regions (referred to herein as homology domain A1 (HDA1; SEQ ID NO.: 1) and homology domain A2 (HDA2; SEQ ID NO.: 2) that together, when operably linked to an hsp68 promoter-lacZ cassette, are capable of enhancing gene expression in a cardiac-specific manner.

Prior art methods of CMG cell isolation are time consuming and produce low cell yields. Generally, cardiomyocytes are detected by their beating. The proportion of beating cardiomyocytes from primary bone marrow stem cells is very low, and even after immortalized CMG cells are established, approximately 70% of cells derived from them are not beating. The failure to achieve a high percentage of beating cardiomyocytes may be due to the incomplete induction of the cardiomyocyte phenotype by 5-azacytidine. Due to the extended time period currently required to isolate CMG cells, it was previously difficult to improve cardiomyocyte induction methods. Beating is one of the last phenotypes to be exhibited by cardiomyocytes. The present invention provides an earlier marker of cardiomyocyte induction. This is useful, for example, for optimizing cardiomyocyte induction methods. By reducing the length of time required for testing, one will be able to more rapidly improve the efficacy of induction of the desired cells. The present invention also provides methods for enriching for cardiomyocytes by, for example, sorting based on expression of a reporter gene operably linked to a Csx/Nkx2.5 cardiac cell-specific enhancer. These and other uses are described in greater detail in the examples.

EXAMPLE 1

Characterization of mCsx/Nkx2.5 Enhancer Elements

As an initial step in defining the regulatory region of Csx/Nkx2.5, we determined the 5' end of the mCsx/Nkx2.5 transcript by 5' RACE with total RNA from hearts of three-week-old mice. Three different transcripts which were identical for most of their length, except for distinct 5' ends, were identified (transcripts I, II, and III). The sequence comparison with the genomic DNA sequence showed exon-intron boundaries in accordance with the consensus exon-intron junction sequences. Therefore, we named the most 5' cDNA segment exon 1a, the most 3' cDNA segment exon 1b, and the intervening genomic sequence intron 1. Likewise, the exon that contains the start codon is termed exon 1c, flanked by introns 2 and 3, and followed by the last exon, exon 2, which includes the homeodomain (HD) and TAG translation stop codon.

Transcript I contains two segments of cDNA at its most 5' end which are discontinuous in the genomic sequence. The most 5' segment of transcript I is 46 bp in length (exon 1a) and is 669 bp upstream from the second discontinuous segment. The second discontinuous segment is 36 bp long (a part of exon 1b) and 3504 bp upstream from the translation start codon. For transcript II, exon 1b is the most 5' sequence and is extended more 5' than in transcript I, in this case 93 bp long, including the 36 bp internal fragment found in transcript I. In transcript III, the first exon at the 5' end, exon 1c, includes 71 bp of continuous genomic sequence which is spliced out in transcripts I and II.

To confirm the existence of the novel exons, we performed primer extension analysis. With adult mouse heart poly(A) RNA, two bands were observed which correspond to the sizes of transcripts II and III. The band representing transcript III was much stronger, suggesting that it is the major site of initiation. Since we could not detect a band corresponding to the transcript I by primer extension analysis, we performed RT-PCR using total RNA samples from several tissues. With exon 1a-specific and exon 1c-specific primer pairs, RT-PCR generated products of the predicted size (112 bp) from the heart and spleen. No band was amplified with RNA from kidney, which does not express Csx/Nkx2.5. By Southern blotting, this 112 bp band was shown to include exon 1b using an exon 1b-specific oligonucleotide probe.

To further characterize the genomic structure of the mCsx/Nkx2.5 gene, we subcloned and sequenced 8.6 kb of genomic DNA. The 3' end of exon 1a is located 4265 bp upstream from the ATG codon, followed by intron 1 (668 bp), exon 1b (93 bp), intron 2 (3179 bp), exon 1c (655 bp) that includes the ATG translation start site, intron 3 (1377 bp), and exon 2 (983 bp) with TAG stop codon and a poly(A) addition signal. The genomic sequences around the three putative transcription initiation sites show no TATA box, indicating that mCsx/Nkx2.5 is a TATA-less gene.

3.3 and 4 kb of 5' flanking sequence drive lacZ expression in the outflow tract and basal portion of the right ventricle as well as in the pharynx, thyroid primordium, and stomach Since the major mCsx/Nkx2.5 transcript (transcript III) starts 325 bp upstream from the ATG codon, we searched for enhancer elements in the genomic region immediately upstream to exon 1c. The 3.3 kb of 5' flanking sequence between the NotI site and the ATG codon was fused to the lacZ reporter gene (CsxlacZ-1; FIG. 1) and injected into mouse embryos to generate transgenic mice. Of 40 embryos examined, eight embryos carried the transgene and three were noted to have β-gal staining. When the lacZ expression was assessed in these embryos at E10.5, we found that this 3.3 kb upstream region could drive lacZ expression in cardiac and extracardiac tissues. Myocardial cells in the outflow tract and the basal part of the right ventricle were strongly positive for lacZ, and there were also a few positive cells in the trabecular layer of the right ventricle. In the outflow tract, lacZ was strongly expressed in the myocardium, but no lacZ expression was detected in the aortic sac or endocardial cushions.

At E10.5, extracardiac expression of lacZ was also observed in locations where the endogenous mCsx/Nkx2.5 was detected, such as the pharyngeal floor, thyroid primordium, and in the distal part of the stomach. In the stomach, lacZ expression was observed in mesenchymal cells. Ectopic expression of lacZ was observed in the surface ectoderm of pharyngeal arches and the laryngotracheal groove. The lacZ expression pattern in both cardiac and extracardiac tissues was substantially identical in all three lacZ-positive embryos, with the exception of an ectopic expression in the glossopharyngeal ganglions in one embryo.

The CsxlacZ-2 construct included the same 3.3 kb of 5' flanking sequence plus 1.4 kb of intron 3 sequence (FIG. 1). Of 34 embryos, six carried the CsxlacZ-2 transgene and, of these, three had positive β-gal staining. Cardiac expression was seen in the basal portion of the right ventricle and in the outflow tract, and extracardiac expression was seen in the pharyngeal floor, the thyroid primordium, and the stomach in two embryos. In one embryo, lacZ expression was noted in the pharyngeal floor but not in other sites. This lack of expression was probably due to a negative effect of the transgene integration site.

The addition of most of intron 1 and exon 1b to the CsxlacZ-1 construct yielded CsxlacZ-3 (FIG. 1). Two embryos were positive for CsxlacZ-3 transgene, with one embryo having positive β-gal staining. The lacZ expression was observed in the outflow tract, right ventricle, pharynx, thyroid primordium, and stomach. Thus, the cardiac β-gal staining pattern was quite similar for constructs CsxlacZ-1, CsxlacZ-2, and CsxlacZ-3. The extracardiac expression pattern was also very similar except for the sites of ectopic expression.

Figure 2:
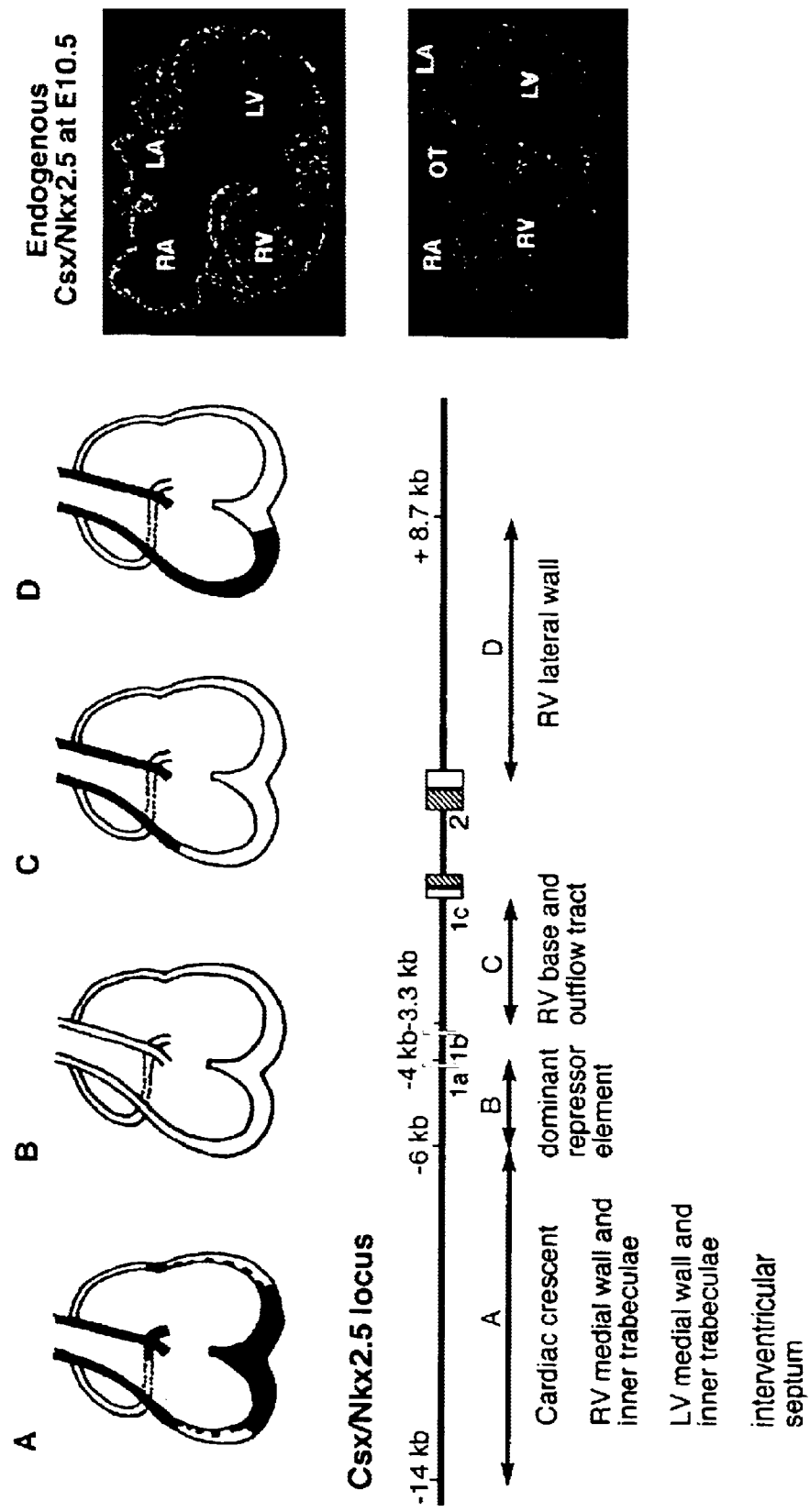
FIG. 2 is a schematic illustration showing a representation of lacZ expression pattern seen in the heart with the mCsx/Nkx2.5 constructs tested.
Figure 3A:
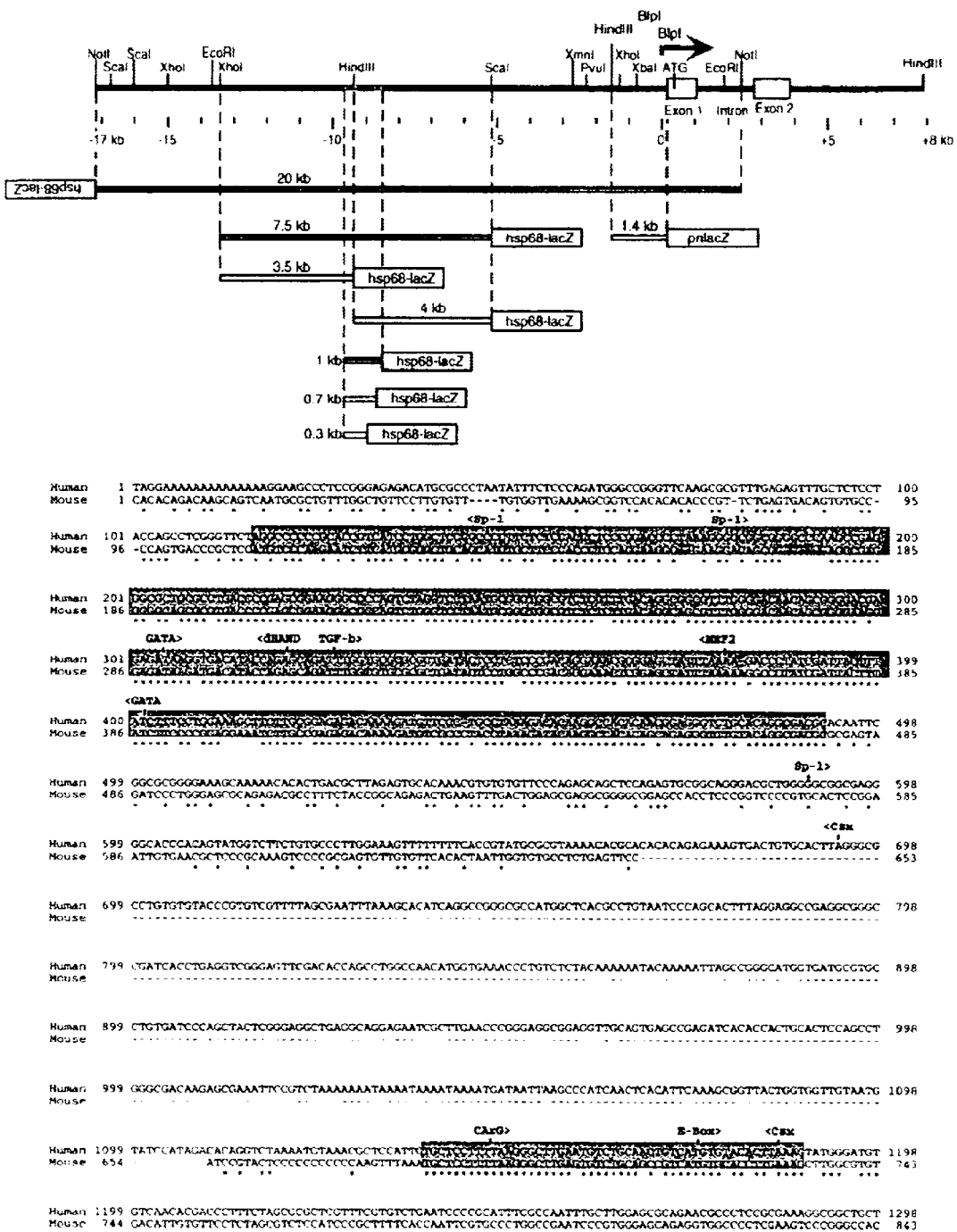
FIG. 3A is an alignment of human Csx/Nkx2.5 (hCsx/Nkx2.5) and mCsx/Nkx2.5 and sequence approximately 9 kb 5' to the ATG of exon 1. Shaded area indicate the location of homology domains A1 (top) and A2. The location of transcription factor binding sites is also indicated.
Figure 3B:
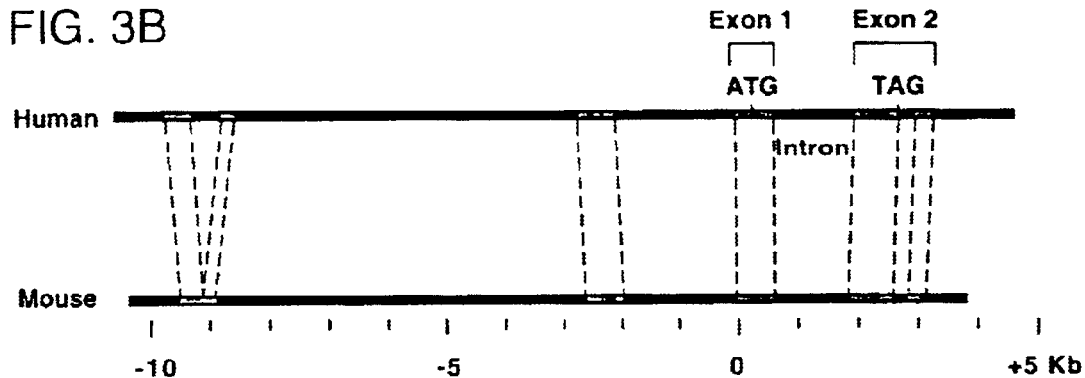
FIG. 3B (top sequence) is an alignment of mCsx/Nkx2.5 and hCsx/Nkx2.5 sequence approximately 3 kb 5' to the ATG of exon 1. Within this sequence is homology domain B (SEQ ID NO.: 6).
Figure 3C:
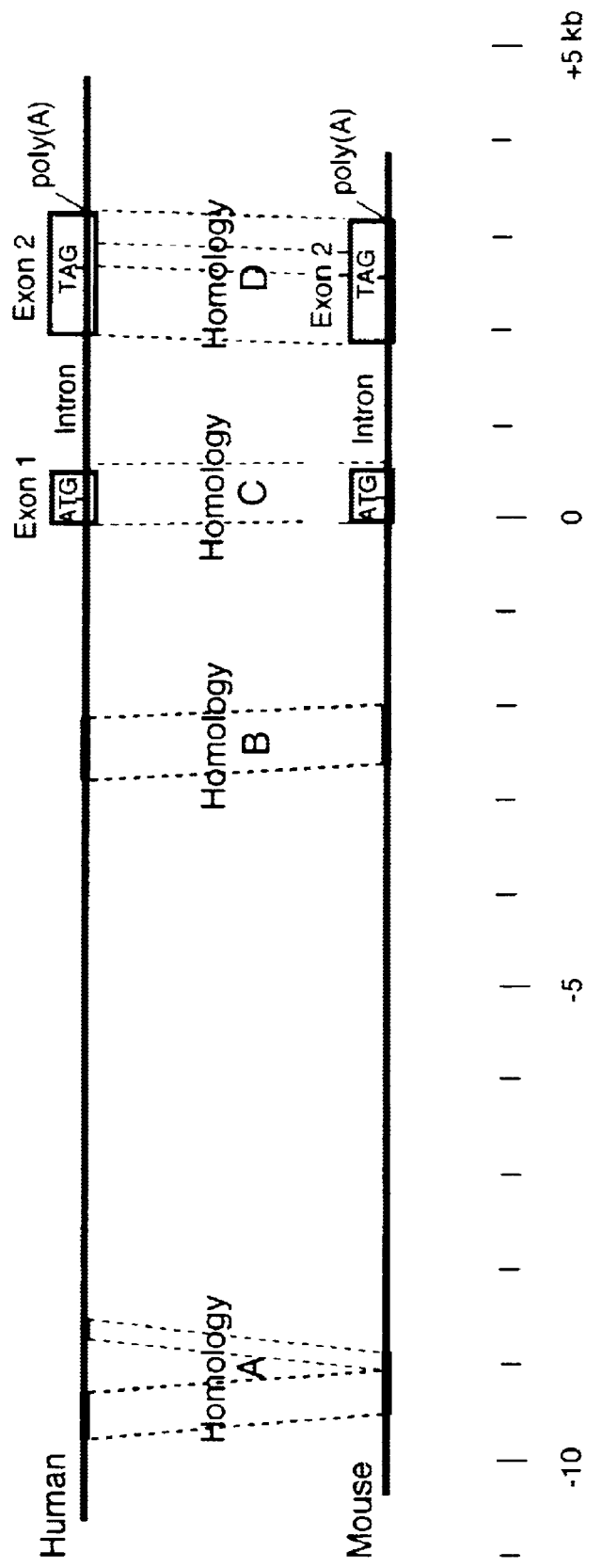
FIG. 3C is a schematic illustration showing the genomic organization of mCsx/Nkx2.5 and hCsx/Nkx2.5. Homology domains A–D are indicated. Note that in homology domain A, the human sequence is interrupted by sequence that has no identity to the mCsx/Nkx2.5 sequence.

CsxlacZ-4 contains 6 kb of 5' flanking sequence. Twenty-two injected embryos were analyzed, and ten found to carry the CsxlacZ-4 transgene. Interestingly, none of the CsxlacZ-4 transgenic embryos showed any β-gal staining in the heart nor in any extracardiac tissues. This finding indicates that a strong negative regulatory element exists between 6 kb and 4 kb 5' to exon 1c (FIG. 2).

A cis-regulatory element for expression of mCsx/Nkx2.5 in the medial wall and inner trabeculae of the right and left ventricles exists between 14 and 6 kb of 5' flanking sequence.

With 14 kb of 5' flanking sequence driving the reporter gene (CsxlacZ-5), lacZ was expressed more widely in the heart than with CsxlacZ-1. β-gal staining was observed in the entire right and left ventricles, except for the compact layer of the lateral walls. In the atrium, there was a cluster of lacZ-positive myocardial cells in the interatrial groove, which is above the future atrial septum. β-gal staining was also seen in the outflow tract as in CsxlacZ-1. Cardiac staining was similar in all four transgenic embryos with positive β-gal staining.

Extracardiac expression of CsxlacZ-5 was observed in the pharyngeal floor and thyroid primordium in all four CsxlacZ-5 transgenic embryos. Only one of the four CsxlacZ-5 embryos was noted to have weak β-gal staining in the stomach, in contrast to strong β-gal staining in the stomach of transgenic embryos harboring CsxlacZ-1, -2, or -3 constructs. No ectopic expression was noted in any of the CsxlacZ-5 embryos, indicating the presence of repressor elements that restrict expression of mCsx/Nkx2.5 in a tissue-specific manner.

An enhancer for the right ventricle is located within 6 kb of the 3' flanking sequence To examine cis-regulatory elements downstream of the coding sequence of mCsx/Nkx2.5, we linked 6 kb of 3' flanking sequence to the CsxlacZ-1 construct to create CsxlacZ-6 (FIG. 1). Of 38 embryos examined, 12 carried the CsxlacZ-6 transgene, of which 6 were lacZ-positive. Three transgenic embryos had β-gal staining in the entire right ventricle, including the compact layer of the lateral walls. The other three had no cardiac staining, but did have weak extracardiac staining. Extracardiac staining in all six embryos included the stomach, pharynx, and thyroid primordium.

Different expression patterns of the reporter gene in adult transgenic mice

In addition to the evaluation of transient transgenic embryos described above, lines of transgenic mice were created and F1 transgenic mice were evaluated at different time points in development.

In the transgenic CsxlacZ-1 line, which carried the 3.3 kb 5' flanking sequence, no β-gal staining could be observed at E7.5. At E9.5, the pattern of cardiac and extracardiac lacZ expression was identical to that seen in the transient transgenic embryos. At E15.5, lacZ expression was also observed in the spleen, but not in the tongue. In the E15.5 heart, lacZ expression was reduced, but detectable in the outflow tract region of the right ventricle, while the transgene expression in the thyroid gland was still strong. Interestingly, when adult animals of the same transgenic CsxlacZ-1 line were analyzed, β-gal staining was completely absent in the hearts.

In the transgenic CsxlacZ-5 line, which carried the 14 kb 5' flanking sequence, β-gal staining was observed in the cardiac crescent at E7.5, in the common ventricle and outflow tract at E8.25, and in the right ventricle, left ventricle, septum, and outflow tract at E9.5. At E15.5, the cardiac β-gal staining was significantly down-regulated, except for patchy expression in the AV junction and in the interventricular septum. The spleen was also stained, but the tongue was not at E15.5. Analysis of adult CsxlacZ-5 transgenic mice showed patchy β-gal staining along the luminal surface of the right ventricle, particularly along the ventricular septal surface. β-gal staining was also seen in a small part of the left ventricle base and in the AV junction area.

Autoregulation of mCsx/Nkx2.5 expression

One of the mechanisms to ensure tissue-specific expression of a transcription factor is a positive autoregulation of its own promoter, as has been shown for the MyoD gene. The mCsx/Nkx2.5 promoter contains multiple NKE elements, the binding sites for Csx/Nkx2.5 protein (Chen and Schwartz, J. Biol. Chem. 270:15628–15633, 1995). In order to determine whether positive autoregulation of mCsx/Nkx2.5 is present, we examined lacZ expression in mice homozygous null mutant for mCsx/Nkx2.5 created by homologous recombination. Since lacZ expression is under the control of 5' and 3' regulatory regions of mCsx/Nkx2.5 in the mutant embryos, β-gal staining will be weaker or absent in homozygous null embryos if positive regulation by mCsx/Nkx2.5 is present. Unexpectedly, β-gal staining was far stronger in the homozygous mutant embryos than in the heterozygous mutant embryos stained simultaneously. These data indicate that a negative feedback, either directly or indirectly, of mCsx/Nkx2.5 exists, since the intensity of β-gal staining in the homozygous mutant heart was much more than double that in the heterozygous mutant heart. To confirm this result, we performed semi-quantitative RT-PCR using RNA extracted from the heart of heterozygous and homozygous mutant embryos at E9.5. Transcripts for lacZ in homozygous mutant hearts were approximately 8-fold those in heterozygous mutant hearts, after adjustment using the relative abundance of the transcript for α-cardiac actin.

The foregoing results were achieved with the following materials and methods.

Isolation of genomic clones and sequencing

Two lambda phage genomic DNA clones containing the mCsx/Nkx2.5 coding and flanking sequences were isolated from a 129 mouse genomic library in λDASH II. Clone 1 contained 14 kb of 5' flanking region in addition to a portion of the mCsx/Nkx2.5 coding region. Clone 2 contained 6 kb of 5' flanking region, the mCsx/Nkx2.5 coding region, and 6 kb of 3' flanking region. In addition, a mouse P1 clone (Genome Systems, St. Louis, Mo.) which contained the mCsx/Nkx2.5 coding sequence, as well as more than 10 kb 5' and 3' flanking sequence, was isolated. Restriction enzyme mapping and serial Southern blotting were performed using standard techniques.

Definition of 5' end of mRNA

5' RACE was performed following previously described methods with some modifications (Reecy et al., Dev. Biol. 188: 295–311, 1997). The first strand cDNA synthesis reaction was performed using 5 μg total RNA from the heart of three-week old mice and 100 ng of random primers (Promega, Madison, Wis.) in a 40 μl volume containing 50 mM Tris-HCl (pH 8.3), 75 mM KCl, 3 mM $MgCl_2$, 10 μM DTT, 40 U RNase inhibitor (Promega), 0.5 mM each deoxynucleotide, 200 U M-MLV reverse transcriptase (Life Technologies, Gaithersburg, Md.) for 90 minutes at 37° C. The cDNA was purified using a QIAQUICK™ PCR purification column (QIAGEN, Santa Clara, Calif.) after incubation with 5 μg RNase A (Ambion, Austin, Tex.). Ligation-anchored PCR was performed as described by Ali Ansari-Lari et al. (BioTechniques 21: 34–36, 1996) with some modifications. Initially, 3 nmoles of a 3' amino-modified 5' phosphorylated anchor primer (5'-TCT CTA CTC CGA ATT CCG TCG TCC ACA CCT-3'; SEQ ID NO: 7) was end ligated to one half of the purified first strand cDNA using 20 U of T4 RNA ligase (New England Biolabs, Beverly, Mass.) in a 50 μL reaction volume containing 50 mM Tris-HCl (pH 8.0), 10 mM $MgCl_2$, 1 mM hexamine cobalt chloride, 20 μM ATP, 25% PEG 800 and incubated for 24 hours at 16° C. The anchor-ligated cDNA was further purified using a QIAQUICK PCR purification column. The first round PCR was performed using one-tenth of the purified anchor-ligated cDNA, an anchor-specific primer (5'-AGG TGT GGA CGA CGG AAT TCG GAG TAG AGA-3'; SEQ ID NO: 8) and a Csx/Nkx2.5-specific primer (5'-GGG GGC GGC TGG GAA AGC AGG AGA GCA CTT-3'; SEQ ID NO: 9). PCR conditions were as follows: denaturation at 94° C. for one minute, annealing at 60° C. for one minute, extension at 72° C. for two minutes with an additional five minutes incubation at 72° C. at the end of the 30 cycles. Subsequent PCR reactions were performed using 5 μl of each PCR product, a nested anchor primer (5'-CGA CGG AAR TCG GAG TAG AGA-3'; SEQ ID NO: 10), and one of the Csx/Nkx2.5-specific primers (5'-TTG AAG GCG GCC AGC ATG CAG GAG GCA-3' (SEQ ID NO: 11) or 5'-ACA GGA GCG ACG GGC AGT TCT GCG T-3' (SEQ ID NO: 12)) at the same PCR conditions as above. The PCR products were visualized on a 2% agarose gel with ethidium bromide, and subsequently subcloned and sequenced.

Detection of exons 1b and 1c by primer extension

Five microgram samples of mouse heart poly(A) RNA were coprecipitated with $2 \times 10^4$ cpm end-labeled, gel-purified oligonucleotide probe (5'-CGG AGC ACC AGG GGC AGA AGA GGC-3'; SEQ ID NO: 13). The samples were resuspended in 10 µl annealing buffer (0.1 M NaCl, 0.01 M, pH 8.0, 0.001 M EDTA), heated to 85° C. for five minutes, the incubated at 37° C. four two hours. Twenty microliters of reverse transcription buffer (10 mM DTT, 16 mM MgCl2, 1 mM dNTP, 1 U/µl RNasin, 0.1 M Tris, pH 8.0) was added to each sample as well as 20 U Superscript™ reverse transcriptase (Life Technologies). Reverse transcription was allowed to proceed at 40° C. for one hour, and 7.5 µl of each sample was mixed with an equal volume of formamide loading buffer. After denaturation at 95° C. for five minutes, 7 µl of each sample was loaded onto an 8% denaturing polyacrylamide gel. After electropheresis, the gel was dried and exposed to film.

Detection of exon 1a by RT-PCR

RT-PCR was performed using rTth DNA polymerase (rTth RT-RNA PCR kit; Perkin Elmer, Branchburg, N.J.) following the manufacturer's protocol. Reverse transcription was performed using an exon 1c-specific primer (5'-ACA GGA GCG ACG GGC AGT TCT GCG T-3'; SEQ ID NO: 14), and the subsequent PCR reaction was performed by adding an exon 1a-specific primer (5'-GAG TGC TCT GCC TGA TGA TC-3'; SEQ ID NO: 15) to the RT reaction according to the manufacturer's instruction. The PCR reaction consisted of 35 cycles of denaturation at 95° C. for ten seconds, annealing/extension at 55° C. for 15 seconds, and, at the end of the 35 cycles, an additional final extension at 55° C. for seven minutes. The PCR products were visualized on a 3% agarose gel with ethidium bromide, and a Southern analysis was performed using a $^{32}$P end-labeled exon 1b-specific primer (5'-CCA GTC TAG AAG CGG TGA TCG CCA-3'; SEQ ID NO: 16).

Construction of reporter gene constructs, generation and analysis of transgenic mice An XbaI-PstI lacZ cassette from pnlacF (Bonnerot et al., Proc. Natl. Acad. Sci. USA 84: 6795–6799, 1987) was subcloned into the XbaI and PstI sites of pBluescript SK- (Stratagene) and regions of the genomic mCsx/Nkx2.5 DNA were cloned 5' or 3' to the lacZ cassette. The CsxlacZ-1 construct included 3.3 kb of genomic sequence, including most of intron 2 and the beginning of exon 1c, between the NotI site and the ATG codon (FIG. 1). An XhoI-PstI fragment containing part of exon 1c, intron 3, and part of exon 2 was subcloned 3' to the lacZ gene in CsxlacZ-1 to make the construct CsxlacZ-2 (FIG. 1). The CsxlacZ-3 construct contains a 4 kb fragment between the SpeI site and the ATG codon of Csx/Nkx2.5, thus including a part of intron 1, exon 1b, intron 2, and part of exon 1c (FIG. 1). CsxlacZ-4 and CsxlacZ-5 contain 6 kb and 14 kb, respectively, of upstream 5' Csx/Nkx2.5 genomic sequence cloned upstream of the lacZ gene. A 6 kb long 3' downstream genomic fragment was fused 3' to the lacZ gene in CsxlacZ-1 to create the construct CsxlacZ-6 (FIG. 1).

For microinjection of CsxlacZ-1, -2, -3, and -6, mCsx/Nkx2.5 genomic sequence together with the lacZ cassette portion of each construct was excised from the vector using XhoI and NotI and purified by gel electrophoresis and Geneclean III (Bio101, Vista, Calif.). In preparation for microinjection, CsxlacZ-4 and CsxlacZ-5 were linearized with XhoI, then purified as indicated above. The creation of transgenic mice was done using standard methods (Hogan et al. (1994) *Manipulating the Mouse Embryo*. Cold Spring Harbor Laboratory Press, New York).

For transient transgenic analysis, $F_0$ embryos were dissected at E10.5. Subsequent genotyping was performed using PCR on chromosomal DNA isolated from the yolk sacs. PCR primer pairs used for detection of the transgenes were as follows: 5'-CCG TCC GAT GAA AAA CAG GAG-3' (SEQ ID NO: 17) and 5'-TCT GCT CTT CGT TGG CTG ATG-3' (SEQ ID NO: 18) for CsxlacZ-1, -2, and -3; 5'-CCG TCC GAT GAA AAA CAG GAG-3' (SEQ ID NO: 17) and 5'-TTA AGT TGG GTA ACG CCA GGG-3' (SEQ ID NO: 19) for CsxlacZ-4 and -5; and 5'-AAC TTG CTA GGT AGA CTA GGC TGG C-3' (SEQ ID NO: 20) and 5'-TCT GCT CTT CGT TGG CTG ATG-3' (SEQ ID NO: 18) for CsxlacZ-6.

Whole-mount β-gal staining was performed according to the method of Schlaeger et al. (Development 121: 1089–1098, 1995). After photographs were taken of the whole mounts, embryos were dehydrated through graded ethanol and xylene, embedded in paraffin, sectioned, and counterstained with Nuclear Fast Red (Vector Laboratories, Burlingame, Calif.).

Generation of mouse lines carrying CsxlacZ-1 and CsxlacZ-5

For CsxlacZ-1 and CsxlacZ-5, we established transgenic lines of mice. The $F_0$ mice carrying each transgene were backcrossed with FVB mice and $F_1$ embryos were examined for lacZ expression. We identified one line of transgenic mice for each construct and analyzed them at different time points, including E7.5, E8.25, E9.5, E15.5, and adult.

Generation of Csx/Nkx2.5 knock-out and lacZ knock-in mice

The entire coding region of mCsx/Nkx2.5 was replaced with a lacZ-neomycin resistance gene (Neo) cassette by homologous recombination in a standard manner (Hogan et al., supra).

In situ hybridization

In situ hybridization was performed as described previously (Tanaka et al., Dev. Genet. 22: 239–249, 1998). Briefly, embryos were fixed in 4% formaldehyde at 4° C. overnight and embedded in paraffin. Tissue sections were hybridized with a $^{35}$S-labeled Csx/Nkx2.5 cRNA probe at 55° C., washed and treated with RNase A. After emulsion autoradiography, sections were counter-stained with hematoxylin and eosin.

EXAMPLE 2

Isolation of hCsx/Nkx2.5 Promoter and Cardiac-Specific Elements

We have cloned an approximately 20 kb-long genomic clone containing about 17 kb upstream flanking sequence, as well as the first exon and a part of intron of the hCsx/Nkx2.5, from a Lambda FIXII genomic library (Stratagene) using radiolabeled hCsx/Nkx2.5 cDNA probes. To narrow down the cardiac enhancer, various regions of the upstream flanking sequence from the 20 kb clone were fused to the hsp68 promoter-linked lacZ reporter, hsp68-lacZ (Kothary et al., Development 105: 707–714 1989) (FIGS. 3A–3C, 6). The expression patterns of these constructs were tested using transgenic mice to define the enhancer region of the cardiac specificity.

Each construct was linearized at immediate 5' end of the subcloned flanking sequence, phenol:chloroform (1:1) and chloroform extracted one time each, alcohol precipitated, and filtered using a 0.22 µm pore size microfilter unit (Eppendorf 5 prime, Boulder, Colo.) after resuspended with deionized water. For transient transgene analysis, $F_0$ embryos were collected at either E9.5 or E10.5, formaldehyde fixed, PBS washed, and examined for the expression of the β-galactosidase. Genotyping was performed using PCR on the chromosomal DNA from the yolk sacs. After the whole body embryos were incubated at 30° C. for 12–14 hour, in X-gal containing buffer, photographs of the lacZ positive embryos were taken. Consequently, the lacZ staining positive embryos were paraffin embedded, sectioned, and counter stained using Nuclear Fast Red. Some of the transgenic mice were established in the whole embryos (at E7.5 and E12.5) or in the hearts (three days after birth) (FIGS. 7–9).

The results of the transgenic study using the constructs described above allowed us to identify an approximately 7.5 kb-long enhancer sequence which showed expression patterns very similar to the mCsx/Nkx2.5 throughout the embryonic development; at E7.5 in the cardiac crescent, at E9.5 in the first branchial arch and the heart, and at E12.5 in the four chambers of the heart including the outflow tract. There was a weak expression of the lacZ also in the stomach region at E12.5. In the three day-old mouse, however, the enhancer activity of the 7.5 kb upstream flanking sequence of the hCsx/Nkx2.5 results in a expression pattern than that observed for the endogneous mouse gene. The 7.5 kb hCsx/Nkx2.5 enhancer-hsp68 promoter-lacZ is active in the right ventricle, but not in the atria or the left ventricle.

We sequenced the 7.5 kb enhancer region of hCsx/Nkx2.5 (FIGS. 4A and 4B), and found regions of high sequence homology between the mouse and the human Csx/Nkx2.5 enhancers (FIGS. 3A–3C, 5A, 5B). When the homologous regions of the hCsx/Nkx2.5 cardiac enhancer (homology domains A1 and A2) were separated from each other, neither part showed enhancer activity. When they were religated by removing the intervening non-homologous sequence, however, the cardiac enhancer activity was regained, implying that both of the homologous regions are required for the cardiac enhancer activity. In these homologous sequences, we found several putative transcription factor binding sites, which are important in cardiac development, such as GATA4, MEF2C, dHAND, SRE, E-box, Sp-1, TGF-b responsive element, and Csx/Nkx2.5 binding sites.

EXAMPLE 3

Figure 10:
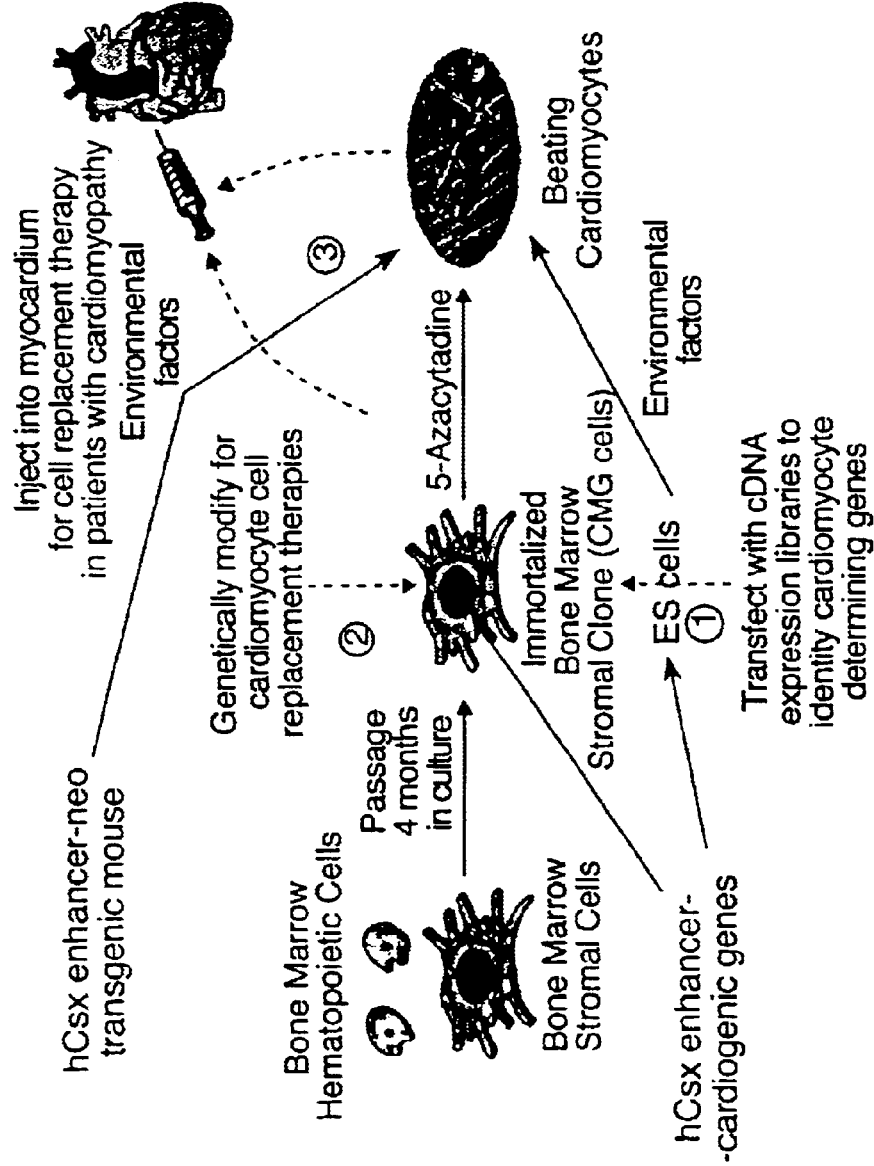
FIG. 10 is a schematic illustration showing various uses of cardiac-specific enhancer elements for facilitating the production or purification of cardiac cells.

Use of Cardiac-Specific Enhancer Elements in the Differentiation and and Purification of Cardiac Cells from Stem Cells Stem cells (e.g., embryonic stem (ES) cells and bone marrow stem cells) are capable of being induced into differentiating into cardiac cells. When mouse ES cells, differentiate as cardiac cells, endogenous mCsx/Nkx2.5 is expressed. Thus it is highly likely that the enhancer elements of the present invention will also be active in stems cells of all types that differentiate as cardiac cells (FIG. 10).

Optimizing induction of cardiac cells

As is described above, current methods for inducing the differentiation of cardiac cells from stem cells have a low efficacy. Thus, in one aspect, the invention features a method for optimizing the efficacy of cardiac cell induction. In one example, a population of stem cells are transformed with a DNA vector that includes a reporter gene (e.g., a gene encoding GFP, β-galactosidase, or alkaline phosphatase) operably linked to a promoter and a cardiac-specific enhancer. Cardiac cell differentiation is then induced by one or more induction methods. Reporter gene expression is determined at the appropriate time: methods that result in a large number or percentage of reporter-positive cells are identified as suitable methods for the induction of cardiac cells. Because reporter gene expression will precede the beating phenotype currently used for scoring cardiac cell induction, the present method can be performed in a shorter time period and at a lower cost than previous methods.

Selecting for or sorting out cardiac cells

As the number of cardiac cells that differentiate from stem cells can very low, the invention also features a method of selecting for cardiac cells (and thereby eliminating non-cardiac cells). In one example of this method, a gene encoding a selectable marker (e.g., neomycin) is operably linked to a cardiac cell enhancer-promoter construct. This construct can be introduced into stem cells or, alternatively, used to produce a transgenic animal (e.g., a transgenic mouse or a transgenic pig), from which stem cells are then isolated. Following induction of cardiac cell differentiation, selection is performed for the appropriate time. During selection, non-cardiac cells die, resulting in an enrichment for cardiac cells.

It is likely that some stem cells express Csx/Nkx2.5 even prior to induction. These cells may have a greater capacity for producing cardiac cells. Accordingly, in another example, the selection step described above is performed prior to the induction step.

In a related aspect, the invention features a method for separating cardiac cells or stem cells having a greater capacity for producing cardiac cells. In this example, the construct is as described above, except that the gene encoding a selectable marker is replaced with a reporter gene that allows for identification of living cells (e.g., GFP). Reporter gene-positive cells can be identified and separated from reporter gene-negative cells using any appropriate method (e.g., fluorescence-activated cell sorting). Again, as in the previous method, the sorting step can be performed prior or subsequent to the induction step.

Augmenting cardiac cell differentiation

Several genes (e.g., BMP2/4, the Wnt family of genes, dHAND, eHAND, MEF-2C, GATA4, SRF, p300, IRX4 and Csx/Nkx2.5) have been implicated in cardiogenesis. Some of these cardiogenic genes are expressed earlier than Csx/Nkx2.5, while others are concomitant or later that Csx/Nkx2.5. Regardless of their temporal expression, it is likely that expression of one of the foregoing genes under the control of a cardiac specific enhancer, such as those described herein, will result in an augmentation of cardiac cell differentiation (i.e., accelerated differentiation, an increase in the percentage of cardiac cells, or both). Therefore, the invention features methods for augmenting cardiac cell differentiation from a population of stem cells by expressing a cardiogenic gene under the control of a cardiac specific enhancer element. Preferably, the method also includes a step in which cardiac cell differentiation is induced (e.g., by introduction of 5-azacytidine).

EXAMPLE 4

Use of Cardiac-Specific Enhancer Elements for Gene Therapy

The use of gene therapy to introduce genes encoding therapeutic proteins, into cardiac cells may be carried out in vivo or ex vivo. Thus, in one aspect, the invention provides a method of modifying cardiac cells of a patient in vivo by inserting into the cardiac cells a DNA vector that includes the gene encoding a therapeutic protein operably linked to a cardiac-specific enhancer of the invention. Nucleic acid molecules are provided in solution or in any other pharmacologically suitable form for administration. Preferably, the DNA vectors are administered directly to the heart, but can also be administered systemically.

There are many delivery methods known in the art for enhancing the uptake of nucleic acids by cells. Useful delivery systems include the Sendai virus-liposome delivery systems (see Rapaport and Shai, J. Biol. Chem. 269: 15124–15131, 1994), cationic liposomes, polymeric delivery gels or matrices, porous balloon catheters (Shi et al., Circulation 90: 955–951, 1994; and Shi et al., Gene Therapy 1:408–414, 1994), intraluminal pressure (PCT/US96/06271, herein incorporated by reference), retrovirus expression vectors, and the like.

The use of liposomes as delivery vehicles is one particular method of interest. The liposomes fuse with the cells of the target site and deliver their contents intracellularly. As noted above, liposomes are maintained in contact with the cells for a time sufficient for fusion, using various means to maintain contact, such as isolation, binding agents, and the like. Liposomes may be prepared with purified proteins or peptides that mediate fusion of membranes, such as those of the Sendai virus or influenza virus, etc. The lipids may be any useful combination of known liposome forming lipids, including, for example, cationic lipids, such as phosphatidylcholine. The remaining lipid will normally be neutral lipids, such as cholesterol, phosphatidyl serine, phosphatidyl glycerol, and the like.

Liposomes may be prepared by the procedure described by Kato et al. (J. Biol. Chem. 266: 3361, 1991). This method allows for the incorporation into the lumen high molecular weight molecules, particularly nucleic acids of one kilobase pair or more. In this way DNA vectors may be introduced into cells efficiently.

In another aspect, cell populations (or organs) can be removed from the patient or donor animal, modified ex vivo by insertion of the DNA vector, and reimplanted into the patient or transplanted into another recipient. Methods for grafting cells into cardiac tissue are described, for example, in PCT publication WO 98/54301. In one example, stem cells are removed from a patient, their number expanded in culture, and then induced to differentiate as cardiac cells as described herein. At any time during the method, the DNA vector including the gene encoding the therapeutic gene may be introduced into the cells. The cells can transplanted into the patient or implanted into a different recipient of the same or different species.

The donor species may be any species which is the same or different from the recipient species, and which is able to provide the appropriate cells (e.g., stem cells capable of differentiating into cardiac cells). The donor may be of a species which is allogenic or xenogenic to that of the recipient. Preferably, the recipient is a mammal, e.g., a primate. Most preferably the recipient is human. For human recipients, it is envisaged that human (i.e. allogenic) as well as pig (i.e. xenogenic) donors will be suitable, but any other mammalian species (e.g., bovine or non-human primate) may also be suitable as donors. For example, porcine aortic endothelial cells (PAEC), or the progenitor cells thereof, can be modified to express the gene encoding a therapeutic protein at effective levels, for grafting into a human recipient.

Heterologous DNA can be inserted into the animal or an ancestor of the animal at the single-cell stage or early morula stage. The preferred stage is the single-cell stage although the process may be carried out between the two and eight cells stages. A transgenic animal can thereby be obtained, which will pass the heterologous DNA onto its offspring.

Gene transfer can also be performed in allografts using ex vivo transduction of cells prior to transplantation, or for xenotransplantation, where porcine transgenesis is established. Methods of preparing transgenic pigs are well known in the art, as discussed by Logan (Curr. Opin. Immunol. 12: 563–568, 2000) and the references cited therein. Any transgenic animal may be used in the present invention; pigs are particularly suitable because they are particularly amenable for xenotransplantation into a human recipient. Transgenic pigs may be produced by homologous recombination and other such techniques that destroy wild type gene function. By way of example, transgenic pigs may be produced utilizing homologous recombination techniques to produce a transgenic animal expressing the desired protein.

For gene delivery, a variety of vectors or plasmids are available (see, Maniatis, et al. (1989) Molecular Cloning: A Laboratory Manual, Cold Spring Harbor, N.Y.; Ausubel et al., *Current Protocols in Molecular Biology*, Greene Publishing Associates, New York, V. 1&2 1996; Harlow and Lane Antibodies, A Laboratory Manual, Cold Spring Harbor Laboratory, 1988, incorporated by reference herein). The common vectors described therein are able to transiently or stably be maintained in smooth muscle cells, usually for a period of at least about one day, more usually for a period of at least about several days.

Retroviral vectors (e.g., lentivirus), and in particular, replication-defective retroviral vectors lacking one or more of the gag, pol, and env sequences required for retroviral replication, are well-known to the art and may be used to transform endothelial or other mammalian cells. PA 317 cells or other producer cell lines producing helper-free viral vectors are well-described in the literature. A representative retroviral construct comprises at least one viral long terminal repeat and promoter sequences upstream of the nucleotide sequence of the therapeutic substance and at least one viral long terminal repeat and polyadenylation signal downstream of the sequence.

Vectors derived from adenoviruses, i.e. viruses that cause upper respiratory disease in humans and are present in latent infections in primates, are also generally known in the art and useful in the present invention. The ability of adenoviruses to attach to cells at low ambient temperatures is an advantage in the transplant setting which can facilitate gene transfer during cold preservation of tissues or organs. Adenoviral mediated gene transfer into vessels or organs by means Of transduction perfusion is also a means of modifying cells in vivo.

Prior to implantation into a recipient species, the treated cells may be screened for modified cells containing and expressing the construct. For this purpose, the DNA vector can also be provided with a second nucleotide sequence encoding an expression product that confers resistance to a selectable marker substance. Suitable selection markers for screening include the neo gene, conferring resistance to neomycin or the neomycin analog, G418. Although any mammalian cell can be targeted for insertion of the gene, the preferred cells for manipulation are stem cells.

All publications cited herein are hereby incorporated by reference.

What is claimed is:

1. A substantially purified nucleic acid molecule comprising an enhancer element having:
   (a) a segment with at least 95% sequence identity to the sequence of SEQ ID NO:1 and a segment with at least 95% sequence identity to the sequence of SEQ ID NO:2;
   (b) at least 95% sequence identity to the sequence of SEQ ID NO:3; or
   (c) at least 95% sequence identity to SEQ ID NO:4.

2. The nucleic acid molecule of claim 1, wherein said element is naturally occurring.

3. The nucleic acid molecule of claim 1, wherein said element is non-naturally occurring.

4. The nucleic acid molecule of claim 1, wherein said enhancer element comprises a binding site selected from the group consisting of Mef2, dHAND, GATA, TGF-β, CarG, E-box, and Csx/Nkx2.5 binding sites.

5. The nucleic acid molecule of claim 4, wherein said enhancer element further comprises an Sp-1 binding site.

6. The nucleic acid molecule of claim 1, wherein said nucleic acid molecule, when operably linked to a promoter, increases activity of said promoter by at least two-fold in a cardiac cell-specific manner.

7. A substantially purified non-naturally occurring nucleic acid molecule having cardiac enhancer activity comprising SEQ ID NO:1 and SEQ ID NO.2, wherein said nucleic acid further comprises a Csx/Nkx2.5 binding site.

8. A substantially purified nucleic acid molecule comprising a cardiac-specific respressor element having at least 95% sequence identity to the sequence of SEQ ID NO: 6.

9. The nucleic acid molecule of claim 1 comprising SEQ ID NO: 4.

10. An expression vector comprising a gene linked to a regulatory sequence wherein said sequence is a cardiac enhancer element comprising:
   (a) a segment with at least 95% sequence identity to the sequence of SEQ ID NO:1 and a segment with at least 95% sequence identity to the sequence of SEQ ID NO:2;
   (b) at least 95% sequence identity to the sequence of SEQ ID NO:3; or
   (c) at least 95% sequence identity to SEQ ID NO:4.

11. The nucleic acid molecule of claim 1, wherein said enhancer element comprises SEQ ID NO.: 3.

12. The nucleic acid molecule of claim 1, wherein said enhancer element comprises SEQ ID NO.: 1 and SEQ ID NO.: 2.

* * * * *

SEQUENCE LISTING

<160> NUMBER OF SEQ ID NOS: 20

<210> SEQ ID NO 1
<211> LENGTH: 375
<212> TYPE: DNA
<213> ORGANISM: Mus musculus

<400> SEQUENCE: 1

| | | | | | |
|---|---|---|---|---|---|
| aggcccccg | caccctcatc | ctggctcccg | cccttctct | ccaccctccc | ggacccctaa | 60 |
| aggggcggcg | gggcccaagc | cgagggcgct | gcgcctgacc | ccgagcggaa | gggcccagt | 120 |
| ctaggtccta | atgcgggtgg | cgtctccttt | gacaggcggc | gtttggggac | aacagcgggg | 180 |
| acgagagata | aggtgacata | ccagagcaga | tttggtgcgc | gcgctgatac | tcctctcccg | 240 |
| acaggaaacg | cggagctatt | taaaagaccc | tatcgattac | tttatctttc | ctggaaagct | 300 |
| tcttgcggag | agacaaaaga | tgttccctgc | ctaaagacac | aaggccacac | aacggagggt | 360 |
| ctgcacaggc | gacgc | | | | | 375 |

<210> SEQ ID NO 2
<211> LENGTH: 51
<212> TYPE: DNA
<213> ORGANISM: Mus musculus

<400> SEQUENCE: 2

| | | | | | |
|---|---|---|---|---|---|
| tgctccttt | aagggcttga | atgtctgcaa | ctgtcatgtg | tacacttaaa | g | 51 |

<210> SEQ ID NO 3
<211> LENGTH: 1072
<212> TYPE: DNA
<213> ORGANISM: Homo sapiens

<400> SEQUENCE: 3

| | | | | | |
|---|---|---|---|---|---|
| aggcccccg | caccctcatc | ctggctcccg | cccttctct | ccaccctccc | ggacccctaa | 60 |
| aggggcggcg | gggcccaagc | cgagggcgct | gcgcctgacc | ccgagcggaa | gggcccagt | 120 |
| ctaggtccta | atgcgggtgg | cgtctccttt | gacaggcggc | gtttggggac | aacagcgggg | 180 |
| acgagagata | aggtgacata | ccagagcaga | tttggtgcgc | gcgctgatac | tcctctcccg | 240 |
| acaggaaacg | cggagctatt | taaaagaccc | tatcgattac | tttatctttc | ctggaaagct | 300 |
| tcttgcggag | agacaaaaga | tgttccctgc | ctaaagacac | aaggccacac | aacggagggt | 360 |
| ctgcacaggc | gacgcacaat | tcggcgcggg | gaaagcaaaa | acacactgac | gcttagagtg | 420 |
| cacaaacgtg | tgtgttccca | gagcagctcc | agagtgcggc | agggacgctg | ggggcggcga | 480 |
| ggggcaccca | cagtatggtc | ttctgtgccc | ttggaaagtt | ttttttcacc | gtatgcgcgt | 540 |
| aaaacacgca | cacacagaga | aagtgactgt | gcacttaggg | cgcctgtgtg | tacccgtgtc | 600 |
| gttttagcga | atttaaagca | catcaggccg | ggcgccatgg | ctcacgcctg | taatcccagc | 660 |
| actttaggag | gccgaggcgg | gccgatcacc | tgaggtcggg | agttcgacac | cagcctggcc | 720 |
| aacatggtga | aaccctgtct | ctacaaaaaa | tacaaaaatt | agccgggcat | ggtgatgcgt | 780 |
| gcctgtgatc | ccagctactc | gggaggctga | ggcaggagaa | tcgcttgaac | ccgggaggcg | 840 |
| gaggttgcag | tgagccgaga | tcacaccact | gcactccagc | ctgggcgaca | agagcgaaat | 900 |
| tccgtctaaa | aaataaaat | aaaataaaat | gataattaag | cccatcaact | cacattcaaa | 960 |
| gcggttactg | gtggttgtaa | tgtatccata | gacacaggtc | taaatgtaa | acgctccatt | 1020 |
| gtgctccttt | taagggcttg | aatgtctgca | actgtcatgt | gtacacttaa | ag | 1072 |

<210> SEQ ID NO 4
<211> LENGTH: 7838
<212> TYPE: DNA
<213> ORGANISM: Homo sapiens
<220> FEATURE:
<221> NAME/KEY: misc_feature
<222> LOCATION: (1)...(7838)
<223> OTHER INFORMATION: n = A,T,C or G

<400> SEQUENCE: 4

```
ctcgagccca ggagttcaag accagcctgg gaaacatagg gagaccctc tctctccaca      60
aaaaatttaa aaactagcca ggtgtggtgg caaacacctg tagtcccagc tactcagaag    120
gctgaggtgg gaggatcact tgagcctgga agtagaggc tacagtgagc cgtgatcaca     180
ccactgcact ccagcctggg agacagagtg agaccctgtc aaataaataa acaaacaaat    240
aatgattaaa ataactaaaa ctaatttat gctattttca ccttgtattt tgtaaagatt     300
tttaaaatga aaattcccaa attgctttcc agaaggattg ttcaaaatta tacccacatt    360
tcactcatgt tctcttcctg aacagcagca atcaggaaaa actccctgga agaggcaggg    420
cttagactga gatttttaaaa gggggtaggc ctcagctctc cttccaggtt tacactgtgc   480
atgtttccaa actcaaagaa tttacactct tctggttgca ttgctctgta aagatctgac    540
ccactactat gtattaaaaa gggatgcatg ataatgaatt cagccctctc tgtaaaatcc    600
aaagggtcct attgcagttt cccccattta atgggtcatt aaaatattct tgggaaggac    660
aaagctttag ttaactatga gaaaacaag cagaaccagc cctggattct gtcttcaaag     720
atttaccat gttggcaggc ctggtagtcc agagcccaag aaaatatccc agccacagat     780
accctagatg tagactagca gtgctacaac ctcaaggtca gaagtatgtc actagaccag    840
agccaaaaat aggtgctata tcattaagag agtaaaaatg caaaccacag acagggtgac    900
attattcaca ataagcatat aacccacagg ggactcctat ctgaatatgc aaagaactct    960
cactaatcaa taagaaaaag gcaaaagatt taaacaggca cttcacaaaa aaagtatatt   1020
caaaaaatca ataaacattt gaaaagatcc tcaattcact agttattagg gaaaggtgaa   1080
ataaaaccac aatgagacac ccccacgccc ccaccagaac ggcttaaaat ctaaacatg    1140
taataccgaa tgttcaag gatgcggaga aactgccatt tttgtacact gccagtatga     1200
gggtaaatct gtacaaccag gttggaaaac gctgagtaga atgtactcta gctggatttg   1260
tgaatatcat atgatccagc aattctactc ctagaaattt acccaacaga aatgtgtaaa   1320
catgttcacc aaaagacaca cgcaagacaa ttcatagagg cactcactat tcctaacagt   1380
caaaaactgg aaactaccca aatgtccatc agcagagaat ggcgataaac agtagcatct   1440
tcacataatg aaatgttttcg acagcaatga aaagtagcta gctacaacta caaacaatgt   1500
gattgaacct cacaaacata tactaagtaa aattatcaga cacaaagagt gtatatactg   1560
tatttagata catgtgaagt ctgaaaacag gcaaaactat tctgttgtta gaagtcagaa    1620
tagttactgc cctgccggga aacagaactc aagagggctt agtagctact ggtaatgttc   1680
tgcttcctga actgcatgct agtgaggcag ctgttatttt gtgcagtcct gtgttacact   1740
ggagttaaaa gttcccccaa aatcagaaag tgttcagcaa gtggaagcaa gtacactgct   1800
ggacttggct gggaacttag gggatcccat aatttgtcac aggcacaagc aaagccagct   1860
ttcttgccnt aagtagcatc tcccagagtc aggatccagg aatggtttgg caggcaggat   1920
gcaaggcagg attcgggagt ggctgagagt tttcccagtg ccacctggtc ccacctcccc   1980
```

```
tctcccactt ctaatgaacg ggcagtacag cttctgttag gaaaagagcc tgggtccta    2040
ggcgatgact gtcacatcta gggagagggc gatgcactgg ggtcctcacc tacaccccc    2100
ttggctgtct caccactctg aattataaat gcccggactt cctcatctcc cacccacaca   2160
tcttgttaga agaaaagaaa cgaatctccc agggctcctt ctaacaaaag tgttcattca   2220
gagtagccct gcttgagggc ccctggcctg gaggagtggg agaggcagcc ctccccctcc   2280
aggagagtca tctccagggc tacccaggac tgagtaacta ggtcaccaga gtaaccaaag   2340
aggcaggaga caagggcatt caagcattgg gccaggaatg gagggtgatg tccagttcat   2400
gttcttctgg ttcagcata gcacacggtg caaatgaacc atcatgcaag aaaacacagc    2460
tagtctccct cctccacca gcaacctttg gttactgata ataatcaaat tcactatttt    2520
tttttttttt taactaaggc tgagataatg tcaaggacc acaggaata ggaaggccta     2580
aaccaaggcc ttaaagaatg agaagaagat tcattcaaaa aagcctccta agggaggaag   2640
atgttttcc ctcctttact tttctacagt aatttttatt ttggataaat aaaccctgat    2700
aaatgagaac ccacgctttc ccaaggccag gctgtgtttt ggtgggtggt cctccgtcag   2760
cagttggagt aatccagagt gatcccgggc aagtcggaag ggagcaagtc tgtgttgaag   2820
ccaagaggta tctttcccta cagcttctca agagaggga tccccgtggg taattgtgag    2880
gctgaaaaca ccgagaggct gactcccatg tttatagagg tcattgatgg gtttgtgcat   2940
ggaaggcagg aggagactga gagtgctttg ttattgttat ttggtttatt tttatttta    3000
aaaaactgga tcagccgact ttgaatacag aaaatgaaaa atgaggagat ttgcataaca   3060
gcgcttggac gtctgaaggg gcccagggcc tagcggctgg tggggcacct agaaacactt   3120
ctgcctgcag atcgcggagg gttagccaca ggaaggggtc gcctaggctg gccacagggc   3180
cttttgctgtg actgaaggac cagccttggc ggcaccttct ttcccctctg ccctgcactc   3240
cggcccccgcc ggagtcagag ctgacttgct gcaggttggg gagaggacag aggctaggac  3300
ggtggcgaaa cctcacctcg tcgcagtccg gaaggtaaac ttggacccgg caggcacttc   3360
ctaaagtcca agctgccctc tctgaagaat aaacctgatt ttcctccgga cgcggacaaa   3420
ggaggattcg ctcacaacta gcctgtaaca aagattccct attttcgtgg ttaggaaaaa   3480
aaaaaaaaag gaagccctcc gggagagaca tgcgccctaa tatttctccc agatgggccg   3540
ggttcaagcg cgtttgagag tttgctctcc taccagcctc gggttctagg ccccccgcac   3600
cctcatcctg gctcccgccc cttctctcca ccctcccgga ccctaaaagg ggcggcgggg   3660
cccaagccga gggcgctgcg cctgaccccg agcggaaggg ccccagtcta ggtcctaatg   3720
cgggtggcgt ctcctttgac aggcggcgtt tggggacaac agcggggacg agagataagg   3780
tgacatacca gagcagattt ggtgcgcgcg ctgatactcc tctcccgaca ggaaacgcgg   3840
agctatttaa aagaccctat cgattacttt atctttcctg gaaagcttct tgcggagaga   3900
caaaagatgt tccctgccta aagacacaag gccacacaac ggagggtctg cacaggcgac   3960
gcacaattcg gcgcggggaa agcaaaaaca cactgacgct tagagtgcac aaacgtgtgt   4020
gttcccagag cagctccaga gtgcggcagg gacgctgggg gcggcgaggg gcacccacag   4080
tatggtcttc tgtgcccttg gaaagttttt tttcaccgta tgcgcgtaaa acacgcacac   4140
acagagaaag tgactgtgca cttagggcgc ctgtgtgtac ccgtgtcgtt ttagcgaatt   4200
taaagcacat caggccgggc gccatggctc acgcctgtaa tcccagcact ttaggaggcc   4260
gaggcgggcc gatcacctga ggtcgggagt tcgacaccag cctggccaac atggtgaaac   4320
cctgtctcta caaaaaatac aaaaattagc cgggcatggt gatgcgtgcc tgtgatccca   4380
```

-continued

```
gctactcggg aggctgaggc aggagaatcg cttgaacccg ggaggcggag gttgcagtga    4440
gccgagatca caccactgca ctccagcctg ggcgacaaga gcgaaattcc gtctaaaaaa    4500
ataaaataaa ataaaatgat aattaagccc atcaactcac attcaaagcg gttactggtg    4560
gttgtaatgt atccatagac acaggtctaa aatgtaaacg ctccattgtg ctccttttaa    4620
gggcttgaat gtctgcaact gtcatgtgta cacttaaagt atgggatgtg tcaacacgac    4680
cctttctagc gcgctcgttt cgtgtctgaa tccccgcatt tcgccaattt gcttggagcg    4740
cagaacgccc tccgcgaaag gcggctgctg atcccgactt tgctccggta tcgcgcagct    4800
tgttggcctc cgggtccccc gtgccatgcc cccgggaggc tctccacaga caccgcttgc    4860
gccgaattat acgagactga atgggttttt ttggtgtgtg tgtgcaacac aacaatttgt    4920
cagctgctgt tcacaatgcg ctccgccggg cggtggaaac ttggctgcgg taacgcacag    4980
caggttggag ggcacgaccc ggaaggaagg aagaggcgag gagggaaagg cggcgaccct    5040
aggcccgctg gccagccgtt ccagcatca attcagcact gagccggccg cagcagcaca    5100
gggctggggg ctcccggaag ttcggccagc cggggtttgg gccagagccg cggaggctgc    5160
ccggtggtag gtgcgactct tcacctctcc ggggagcggc ggccgacgac ccaacccacc    5220
cgcaagcgct gccgtcggcc cggctggtcc cccgcgcggg cacaaaaaca ggcggcagtt    5280
cgccagctct cttttcccaa acctgaaccg ccaagccgaa ggttcttcca aagtcgcggt    5340
tccccgggct tcacacccgc cgggcaggcg cgaaccagcc ccaggacaac cattttcctc    5400
ttcactgtat ctgagtcgtt gtccatctga ctcgaatgtc acctgatttt cccagctgtg    5460
acctccagcg acgggactcc gaggaactga ttccagcgtc tcgattctct ccgcctctcc    5520
gcccgttttg gctgaagcgg tttgcagccg tcggggcaga aggggtggga tgtggcagcc    5580
accagcccca gcccagagaa gaaaagagga cgaaattaac gcgaaaggac accggaagtc    5640
tgaaagcgac tccctcggat cctcggaatc cgaggcaaac cctaacacta gtttgaaagc    5700
ggatcatatc cactaatcca ggacaaattc gggttgggaa acatactccc cagagcctaa    5760
gaaaactgac ttcaacaaa acaaaactga caaggacaaa atgcaaagga gtttgtgaaa    5820
cgtaattgct ctcagaaaat atgtgtatat atatacatcc tataatatgt tttaaatttg    5880
caaaaaaaaa gtctctaaga ggatatattt ttaaaaccag tggcagcttg ggagggagtg    5940
gggattagct gagaagggga gaaggaagca ttttgaggt gacgtaaatg ttttttgtatc    6000 ttgattatgg tggctgttat gggggtgcac atccaagtgt caagactcat cgaactgtac    6060
acttttgttc taggtacatt agacctcaat aaagtggatt ttaaacctaa ataagccagg    6120
taacagcttt gcctgggtgg ctgggggaga ggcttgggac actttacatt gatctccctc    6180
ttaggcatgt tcgttttggt ttggttttgt tcttatgatg tattatttat tcaaaaatat    6240
atcattagca gagtgactga tgtaaatgta aaccattgt taaggaaacc aacaaaagcg    6300
ggaacaagag acactggtgc atcctgttag agggataaga ataagcactc gctgtccaag    6360
ctcataaaat attttgggaa tgaatgtcgt tccgctttgt ttttttggtt ttttgctca     6420 tgtgtttaac atcaacgaga atgaggacc caaaacttat ccagtggtta cgtgtggtgt    6480
gtgtggctgt catctccttg ggactggcta ctgaaggcca caggcgtggg aggaccaaat    6540
gctccctgga tgttgagtcc cagccggtaa gcagcacaca gtcccgcttg cagcaaagat    6600
gtggtggccg gctgcgctgt gggggaaggc caggcccgga caggaacctc agatctcacc    6660
ggcggatgag agtggtgccc cctgcagctg gagtccctgc tggcctgaga gctccagctg    6720
```

```
tgccaccgtt gggcagaccc cacacttcag ggagctgcca ggatcagtgg ctacaagagt    6780 cccccaccgtg tttggagaaa ctaggtatga aatatttcca tttacacccc taccccggcc    6840
ccagacagga aagtcacttc aaccttgtta ggtcagattc cagatctggt tcagatgcag    6900
ggctatttca gagagatttt tagaggctga ctctcaggag agggaaggac agtgggctga    6960
aggccagggg tcaggaaatc taggaactgc taaactcctc tgctggcctg cggggagcgc    7020
ccgggtgggg ctaccaaggc cacaagccag ttccatcttc ccactttgcc accttctcac    7080
agggaccagg ctctgcatcc tcagtgacca aagacttgg gcctgccctc tagtttgtct    7140 ataccctgccc cctcccttga ctcatactgt ccaagacccc aagaccaaac cacaagtcag    7200
gagagatctt gagggcagcc agtgccacca gggtcctgtt cccaggtact actagacaaa    7260 ggccacccctt cctcccctct ctctagggct ccgctgacca ccctgcacag tcttcctaca    7320
ccaagggctc cggtgccacc ccttcacaga gagttcactg caccgctgct tcggctgcct    7380
gtctcaaacc atacacacac ctttgattct taaactccaa gattaggatg ggccccagaa    7440
atctgcattt ttaatatgta cctcagagga ttctggccta gatatttcta cagccccaaa    7500
agtaacaagg aacctgttcc aaaaagtgta ttacggaaac tgtcatgttt attcttgact    7560
tgccccccaa ttattcttcc cctgaagttt tcatcaccaa aaacccccac atgtgaacca    7620
tatgtgtaca tatgcccata tttaaaatac aaattctgca cctggtttgc tatttaaagt    7680
atctcaaaac atatccataa gaatacatat gaatggaact aattctttct catgggatat    7740
gggatctgtt ctatggacaa cataattttt aaccagtcct agtatatata cactggtttt    7800
ttacatgttg atcttaaaaa ataaaaacgg ntgaaann                             7838

<210> SEQ ID NO 5
<211> LENGTH: 6751
<212> TYPE: DNA
<213> ORGANISM: Homo sapiens
<220> FEATURE:
<221> NAME/KEY: misc_feature
<222> LOCATION: (1)...(6751)
<223> OTHER INFORMATION: n = A,T,C or G

<400> SEQUENCE: 5
caatttctat tnagttctat taaaagggat ttttttttnaa ctcactggna accaggagga     60
ctgnaaagaa aagtgaaatg gctctgggac tttcctctaa ggagaccagc atgggtcgcc    120 ccaatttta ttttgcacgt atttgtccgt ttttgcccca tctcctctct cctgaaacac    180
caagaccttt ttgaagcca agagaaatca ttacccgatt cacaaagagc atagagagtg    240
taacagtcac tgatcttgtt caaataggga gagttttttt tccttcccct tttgtaacac    300
ctgacccaca ggactgacag ttctaggaag cccccttacc cgaaaatagg aaataaatcc    360
ttgccacctt gatttgcaag ggcaatgcta atttttttct ttctccagag ctctcaaaaa    420
aaaaaaaaaa aaaccttac taaaaacagg gatcccggat gtagcctcga tgtcccccat    480
taaacggtaa tatttcaggc gtccgctcac actaatcttt caaactgtca tcgcgagccg    540
cctggccagc agattcactt aacagcgctc ccaggaccct cgttccgagc tcttttcagc    600
gagacattta attgaatcgg atgtggctcg tttgccagac gtcaccgcct cggcgatagg    660
catcctctcc aacgacaccc ccccgccc gcgctcgaaa acaatcttca aaaggcaagg    720 gggccccccca agtaggttaa tttacaacca taacggtaac gtggccaaaa gncaggcgag    780
gaagggccgc aaggccgctg acatgcaagc tccgtccaag aagaatttgg gttggaggtg    840
aagaggtggg gggacgaggt ttcntgggcc ttgaacgccc cacatttaaa aaaggcatcc    900
```

```
tccacagact agactaacaa ttccagaccc ccagtagtcc ctggctcaga aactcgaggc    960
gtgatttcgg cgtggcagcc caggcctgtt actgacggct ggcgcctaga agccggggtc   1020
agggcgttgc gcgcctcctg ggctgccctg cggggctcac ctctctcccc agcatggagg   1080
ccccaggtcc tgggagtgtg gctttgatga gggacaggaa aagtcccaac atcaggccaa   1140
tgcttgactt cacttgcgtc ggcgtctcag acggcacact gtcgggtttg agcacccaag   1200
atgtacgttc tggacagaca ctattttgtc cccatacatg gagcgtttcc tccgcacctt   1260
gggcgcgcct gcgggagctg tgtctttagg tagttttttgg ccctgcgccg cctttattct   1320
actccaagcg ctctttgcca aacccgcact ccgcaaagag ccaagccctc cacatcccca   1380
ttctcagcaa gtccacgcgt cccgcccagc ttcccgcccg cggttccctg taccagctag   1440
ggccgtgaga agccaacgct tttccactga caaatcctgt catccccagc tctagaaggc   1500
gtccttaacc tgggcccgct ctgcctgccc ggactcctga attgtaagca aaataaaact   1560
cctctctgca gtgttctggg aatggagaa gaccccaagc tttcatcaga ccctcccaag    1620
gagtgcgggg acccagagaa atgaggccac ccgggcagga tctggccatg tagctggcgc   1680
tcctgaaact ctggcagatt tgtctgactt ctgtgcccta ctctactgac cctgggctaa   1740
aaatgatcat gatcacccca cttgccctgc ccttccccca cgcgcctgac cgagccgcag   1800
gggtgcccca ctgaagtcc ggcccagagg cctcagagaa atcctggcct agctgggctc    1860
agaggagccc cgcctccctg agagctaaac ctgggctagg accctgaaac ctcgaggttg   1920
gcagaagcct gagggccttg ctgccaggca ggagggcac gggaaggagg gaggtgggat    1980
cgatggcctc caaacagggg aaacaaggtg gctggtagct ggggcactcc acaagacagg   2040
tgtntcctgg gaagctgagc ttaccagctg ggattcctga tttatttcat tattaagggg   2100
agaggcattt ccctgggag ggtactggca gtgactgatg cccctggag ttgtgctgtg     2160
cataacacta ctgtaggagg cagcaactcc taccccacct ggccatcact cacccttgccc   2220
ttactttcgt tgattcgccc agaagcaccc agagcctgcg gcatgattga ccctgtaggc   2280
caagccaaac caaacccccg aattgtccag aattttcgcc ctggtgtatc cccaaagccc   2340
agccctgtct ttnagggttt ttttcctatt gagattttcc ctcatcccac cacctttagt   2400
aataaagcct tcctcaaact aatttcctcc ccaccgcttc ccaccccatc cttttttttt   2460
cccatgctgg tttgggtgct gaggaatatt ttttcaaacc cacacccatc cagccctgcc   2520
cagaggcctg actttgcatg cctctggtag gnttttcagg gttacattag ggagcaaaag   2580
cagggtgcag gggcaaaagg ggaccccttcc aaatgggtcg tggccccttt aaaaaagctg   2640
ggcagggntt tttttttttt tttttttttt tttttttttt tttttttgccg tatgactata   2700
ttaggtgaca cgaaactgct catcgctcct gtcatcgagg cccctggccc aatggcaggc   2760
tgagtccccc tcctctggcc tggtcccgcc tctcctgccc cttgtgctca gcgctacctg   2820
ctgcccggac acatccagag ctggccgacg ggtgcgcggg cggcggcgg caccatgcag    2880
ggaagctgcc aggggccgtg ggcagcgccg ctttctgccg cccacctggc gctgtgagac   2940
tggcgctgcc accatgttcc ccagccctgc tctcacgccc acgcccttct cagtcaaaga   3000
catcctaaac ctggaacagc agcagcgcag cctggctgcc gccggagagc tctctgcccg   3060
cctggaggcg accctggcgc cctcctcctg catgctggcg gccttcaagc cagaggccta   3120
cgctgggccc gaggcggctg cgccgggcct cccagagctg cgcgcagagc tgggccgcgc   3180
gccttcaccg gccaagtgtg cgtctgcctt tcccgccgcc cccgccttct atccacgtgc   3240
```

```
ctacagcgac cccgacccag ccaaggaccc tagagccgaa aagaaaggtg aggaggaaac    3300
acaggccccc ttctcccctc ctgggtcgct ttcgtcccca agaaactcag ggccaggagg    3360
aggacacacg cgcccttggg ccgagggctg ggctgcggcg gggggttcag aatgtaagat    3420
gcctggtgtt gtcgccaggc tcccgcgccc cgcgtccaat cggaggttca gaggaaatgc    3480
cggattgaaa ggatccgaaa gcaagagacc aaaaaacttt tcccccggc ctaacaaacc     3540 cccggcggtt tccgctctgc tcctggttct ggtagaattt taaaaatcgg tttatggtta    3600
aacaaaacaa aaaaacagcc aaaaccccg tttttaccc ccccttgga ttttcaaacc       3660 cttttttaaaa tttttgaaaa aaaccccca aacaaaatta aattttttcc cccaaaaaat    3720
tttttttttt aacaaaaggg ggggtggaaa attttttttt tccccccccc aaaagggggtt  3780 tttgttttt tttttttntt tggcaaaaat gaattntgga ncnaggcctt atttaaatg      3840 gatattgggn ccncaggatt ttgatttcat ttattttttt aagcaaactt nccgggccgg   3900 caagggaaa ggttccctcg tgaaaagta ggaaatgctg cgctaccgcg ggcacaaggn      3960
agtggacgag atgagtgcgg gatcatcccg caggccatcc caggatcggg gagggaggcc   4020
ggccccgctg cagaaagggg cttctgggag accccccagc ccaaggcagg agcccgggcg   4080
attcccggga ggccgcaggc gctgggcgaa gcgctgggcg aagggccgct gccagccggg   4140
agagaattca taggtttgtt gaggagcaga ggcctgggaa caaattcggg cgggcacggc   4200
ggctagaact gatcgctacc aattcgagga agccagcaag gcaggttccg aggccgcctg   4260
cccacccgca gcttcttgga cactgcgcaa accctgctgc ggccaggctg gagcctccga   4320
tcaccaaacc aacactccct ggccttctgt ttcttgattc cttaattttg agataagacc    4380
gtccctagca gtgaggcctc ggcctctgtt catttaactt ctcaaaccaa actagcccta   4440
attcagttca ccccagagca tcacctggtt ttatttttat ttttttattt tttatttat    4500 tttttttttt tttgcagcct gaaattttaa gtcaccgttt gtctccctca ccagggtgtg   4560
aactgccccg agggcagaga cctcccgttt tgttttccag cgccttgagc cagcttgact   4620
ttttacaaat gctgagtgag acgtgtcggt ggctcccagt gcacttggca gagtgagccg   4680
cagccagctg ggcgctccag gcaggacaca gtggcctcca cgaggatccc ttaccattac   4740
tgtgcggccg cgctccgtag gtcaagccgc tcttaccaag cgtctttctg cctttctgtt   4800 cccctcaga gctgtgcgcg ctgcagaagg cggtggagct ggagaagaca gaggcggaca    4860
acgcggagcg gccccgggcg cgacggcgga ggaagccgcg cgtgctcttc tcgcaggcgc   4920
aggtctatga gctggagcgg cgcttcaagc agcagcggta cctgtcggcc cccgaacgcg   4980
accagctggc cagcgtgctg aaactcacgt ccacgcaggt caagatctgg ttccagaacc   5040
ggcgctacaa gtgcaagcgg cagcggcagg accagactct ggagctggtg gggctgcccc   5100
cgccgccgcc gccgcctgcc cgcaggatcg cggtgccagt gctggtgcgc gatggcaagc   5160
catgcctagg ggactcggcg ccctacgcgc ctgcctacgg cgtgggcctc aatccctacg   5220
gttataacgc ctaccccgcc tatccggggtt acggcggcgc ggcctgcagc cctggctaca   5280
gctgcactgc cgcttacccc gccgggcctt cccagcgca gccggccact gccgccgcca   5340
acaacaactt cgtgaacttc ggcgtcgggg acttgaatgc ggttcagagc cccgggattc   5400
cgcagagcaa ctcggggagtg tccacgctgc atggtatccg agcctggtag ggaagggacc   5460
cgcgtggcgc gaccctgacc gatcccacct caacagctcc ctgactctcg tggggagaag   5520
gggctcccaa catgaccctg agtccctgg attttgcatt cactcctgcg gagacctagg    5580 aacttttttct gtcccacgcg cgtttgttct tgcgcacggg agagtttgtg gcggcgatta   5640
```

-continued

```
tgcagcgtgc aatgagtgat cctgcagcct ggtgtcttag ctgtccccc aggagtgccc      5700 tccgagagtc catgggcacc cccggttgga actgggactg agctcgggca cgcagggcct      5760
gagatctggc cgcccattcc gcgagccagg gccgggcgcc cgggcctttg ctatctcgcc      5820
gtcgcccgcc cacgcaccca cccgtattta tgtttttacc tattgctgta agaaatgacg      5880
atccccttcc cattaaagag agtgcgttga ccccgcacgt gtgcttcttt cagcttgcgg      5940
cgcttcagaa gcaggagaga ggtggccgcc cgggactggt ctcagatctc aggcacaggc      6000
attccctgag caaattgata acattgatac taataaaacc taacccttgc tggaaccata      6060
ctggttccgt gtcgggcact ttctgagatt gtctcatata atcctcaata atccaaaaaa      6120
aaaaaaatcc taaagtttag aagctgaggc ccggagaggt ttaatgactt acctgcgagc      6180
aaatagccag tactagtcga actctggtta aattcaggat gcctcacttc agagaccgcc      6240
ttccctgtgc tcccaagctc ccctccttga atcctaatgt gtgccaggca cggttccagg      6300
cactgggcat taaatggaca agcaaaagaa cctgggccct ctgtagctgg agagcaccgt      6360
gatcatccca cttaaaagaa ctccttaacc tgtttccaag atggnaaaag ccaagaancc      6420
aaagcccttg ggnaagcgtt ctcaagggtc ctcanatgcc ccaaatgcca cgtcggggc       6480 tcaacanctn gcccgttgga actgaatgcc nanggtgggc cccaaanaag gntcctgcgg      6540
gatggngctc aactccaagc tgtggtgaag gcccataaaa ttcaaatggg ccaaggggag      6600
cccctaaaag ccctaaacct tcnggggtc cnttccctaa gggcatttaa ntttaccaaa       6660
agtttggnca aanaatgttt ccaatggncc ngattttatn gangggnaaa actggnggc       6720 aaccgaaatc cagtttaaac ccgggttgtt t                                     6751
```

<210> SEQ ID NO 6
<211> LENGTH: 478
<212> TYPE: DNA
<213> ORGANISM: Homo sapiens

<400> SEQUENCE: 6

```
agagaaatca ttacccgatt cacaaagagc atagagagtg taacagtcac tgatcttgtt        60
caaataggga gagttttttt tccttccctt tttgtaacac ctgacccaca ggactgacag       120
ttctaggaag ccccccttacc cgaaaatagg aaataaatcc ttgccacctt gatttgcaag      180
ggcaatgcta attttttct ttctccagag ctctcaaaaa aaaaaaaaa aaaaccttac         240 taaaaacagg gatcccggat gtagcctcga tgtcccccat taaacggtaa tatttcaggc      300
gtccgctcac actaatcttt caaactgtca tcgcgagccg cctggccagc agattcactt      360
aacagcgctc ccaggaccct cgttccgagc tcttttcagc gagacattta attgaatcgg      420
atgtggctcg tttgccagac gtcaccgcct cggcgatagg catcctctcc aacgacac       478
```

<210> SEQ ID NO 7
<211> LENGTH: 30
<212> TYPE: DNA
<213> ORGANISM: Mus musculus

<400> SEQUENCE: 7

```
tctctactcc gaattccgtc gtccacacct                                         30
```

<210> SEQ ID NO 8
<211> LENGTH: 30
<212> TYPE: DNA
<213> ORGANISM: Mus musculus

-continued

```
<400> SEQUENCE: 8
aggtgtggac gacggaattc ggagtagaga                                     30

<210> SEQ ID NO 9
<211> LENGTH: 30
<212> TYPE: DNA
<213> ORGANISM: Mus musculus

<400> SEQUENCE: 9
gggggcggct gggaaagcag gagagcactt                                     30

<210> SEQ ID NO 10
<211> LENGTH: 21
<212> TYPE: DNA
<213> ORGANISM: Mus musculus

<400> SEQUENCE: 10
cgacggaart cggagtagag a                                              21

<210> SEQ ID NO 11
<211> LENGTH: 27
<212> TYPE: DNA
<213> ORGANISM: Mus musculus

<400> SEQUENCE: 11
ttgaaggcgg ccagcatgca ggaggca                                        27

<210> SEQ ID NO 12
<211> LENGTH: 25
<212> TYPE: DNA
<213> ORGANISM: Mus musculus

<400> SEQUENCE: 12
acaggagcga cgggcagttc tgcgt                                          25

<210> SEQ ID NO 13
<211> LENGTH: 24
<212> TYPE: DNA
<213> ORGANISM: Mus musculus

<400> SEQUENCE: 13
cggagcacca ggggcagaag aggc                                           24

<210> SEQ ID NO 14
<211> LENGTH: 25
<212> TYPE: DNA
<213> ORGANISM: Mus musculus

<400> SEQUENCE: 14
acaggagcga cgggcagttc tgcgt                                          25

<210> SEQ ID NO 15
<211> LENGTH: 20
<212> TYPE: DNA
<213> ORGANISM: Mus musculus

<400> SEQUENCE: 15
gagtgctctg cctgatgatc                                                20

<210> SEQ ID NO 16
<211> LENGTH: 24
<212> TYPE: DNA
<213> ORGANISM: Mus musculus
```

```
<400> SEQUENCE: 16
ccagtctaga agcggtgatc gcca                                              24

<210> SEQ ID NO 17
<211> LENGTH: 21
<212> TYPE: DNA
<213> ORGANISM: Mus musculus

<400> SEQUENCE: 17
ccgtccgatg aaaaacagga g                                                 21

<210> SEQ ID NO 18
<211> LENGTH: 21
<212> TYPE: DNA
<213> ORGANISM: Mus musculus

<400> SEQUENCE: 18
tctgctcttc gttggctgat g                                                 21

<210> SEQ ID NO 19
<211> LENGTH: 21
<212> TYPE: DNA
<213> ORGANISM: Mus musculus

<400> SEQUENCE: 19
ttaagttggg taacgccagg g                                                 21

<210> SEQ ID NO 20
<211> LENGTH: 25
<212> TYPE: DNA
<213> ORGANISM: Mus msuculus

<400> SEQUENCE: 20
aacttgctag gtagactagg ctggc                                             25
```